(12) United States Patent
Chatelier et al.

(10) Patent No.: US 8,877,034 B2
(45) Date of Patent: Nov. 4, 2014

(54) SYSTEMS, DEVICES, AND METHODS FOR MEASURING WHOLE BLOOD HEMATOCRIT BASED ON INITIAL FILL VELOCITY

(75) Inventors: Ronald C. Chatelier, Bayswater (AU); Dennis Rylatt, Wheelers Hill (AU); Linda Raineri, Prahran (AU); Alastair M. Hodges, Blackburn (AU)

(73) Assignee: LifeScan, Inc., Milpitas, CA (US)

( * ) Notice: Subject to any disclaimer, the term of this patent is extended or adjusted under 35 U.S.C. 154(b) by 239 days.

(21) Appl. No.: 12/649,509

(22) Filed: Dec. 30, 2009

(65) Prior Publication Data

US 2011/0155584 A1 Jun. 30, 2011

(51) Int. Cl.
*G01N 33/49* (2006.01)
*G01N 33/80* (2006.01)
*G01N 33/48* (2006.01)
*G01N 27/48* (2006.01)

(52) U.S. Cl.
CPC ............... *G01N 33/80* (2013.01); *G01N 27/48* (2013.01); *G01N 33/49* (2013.01)
USPC .................. 205/777.5; 204/403.01; 422/68.1; 422/82.01; 435/287.1; 205/792

(58) Field of Classification Search
CPC ........ G01N 33/49; G01N 33/80; G01N 33/26
USPC ............. 204/403.01–403.15; 205/777.5, 778, 205/792; 600/345–348; 422/68.1, 82.01; 435/287.1
See application file for complete search history.

(56) References Cited

U.S. PATENT DOCUMENTS

| 5,385,846 A | 1/1995 | Kuhn et al. |
| 5,620,579 A | 4/1997 | Genshaw et al. |
| 5,653,863 A | 8/1997 | Genshaw et al. |

(Continued)

FOREIGN PATENT DOCUMENTS

| CA | 2 309 280 | 6/1999 |
| CN | 1558224 A | 12/2004 |

(Continued)

OTHER PUBLICATIONS

Australian Notice of Acceptance issued Oct. 27, 2011 for Application No. 2010257465.

(Continued)

*Primary Examiner* — Jennifer Dieterle
(74) *Attorney, Agent, or Firm* — Hiscock & Barclay, LLP

(57) ABSTRACT

Methods for determining the hematocrit of a blood sample, and devices and systems used in conjunction with the same. The hematocrit value can be determined on its own, and further, it can be further used to determine a concentration of an analyte in a sample. In one exemplary embodiment of a method for determining the hematocrit value in a blood sample, a volume of blood is provided in a sample analyzing device having a working and a counter electrode. An electric potential is applied between the electrodes and an initial fill velocity of the sample into the device is calculated. The hematocrit of the blood, as well as a concentration of an analyte in view of the initial fill velocity can then be determined. Systems and devices that take advantage of the use of an initial fill velocity to determine hematocrit levels and make analyte concentration determinations are also provided.

12 Claims, 11 Drawing Sheets

(56) References Cited

U.S. PATENT DOCUMENTS

| | | |
|---|---|---|
| 5,781,455 A | 7/1998 | Hyodo |
| 5,858,648 A | 1/1999 | Steel et al. |
| 5,942,102 A | 8/1999 | Hodges et al. |
| 6,174,420 B1 | 1/2001 | Hodges et al. |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,379,513 B1 | 4/2002 | Chambers et al. |
| 6,413,410 B1 | 7/2002 | Hodges et al. |
| 6,424,847 B1 | 7/2002 | Mastrototaro et al. |
| 6,475,360 B1 | 11/2002 | Hodges et al. |
| 6,475,372 B1 | 11/2002 | Ohara et al. |
| 6,521,110 B1 | 2/2003 | Hodges et al. |
| 6,576,117 B1 | 6/2003 | Iketaki et al. |
| 6,599,407 B2 | 7/2003 | Taniike et al. |
| 6,632,349 B1 | 10/2003 | Hodges et al. |
| 6,638,415 B1 | 10/2003 | Hodges et al. |
| 6,676,995 B2 | 1/2004 | Dick et al. |
| 6,749,887 B1 | 6/2004 | Dick et al. |
| 6,780,645 B2 | 8/2004 | Hayter et al. |
| 6,797,150 B2 | 9/2004 | Kermani et al. |
| 6,830,934 B1 | 12/2004 | Harding et al. |
| 6,856,125 B2 | 2/2005 | Kermani |
| 6,869,411 B2 | 3/2005 | Langley et al. |
| 6,872,298 B2 | 3/2005 | Kermani |
| 6,895,263 B2 | 5/2005 | Shin et al. |
| 6,946,067 B2 | 9/2005 | Hodges et al. |
| 7,043,821 B2 | 5/2006 | Hodges |
| 7,045,054 B1 | 5/2006 | Buck et al. |
| 7,132,041 B2 | 11/2006 | Deng et al. |
| 7,195,704 B2 | 3/2007 | Kermani et al. |
| 7,199,594 B2 | 4/2007 | Kermani |
| 7,288,174 B2 | 10/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,431,820 B2 | 10/2008 | Hodges |
| 7,452,457 B2 | 11/2008 | Burke et al. |
| 7,488,601 B2 | 2/2009 | Burke et al. |
| 7,491,310 B2 | 2/2009 | Okuda et al. |
| 7,597,793 B2 | 10/2009 | Burke et al. |
| 7,749,371 B2 | 7/2010 | Guo et al. |
| 7,771,583 B2 | 8/2010 | Diamond et al. |
| 7,923,258 B2 | 4/2011 | Heller |
| 8,101,065 B2 | 1/2012 | Chatelier et al. |
| 2002/0150896 A1 | 10/2002 | Polonsky et al. |
| 2003/0155237 A1 | 8/2003 | Surridge et al. |
| 2003/0180814 A1 | 9/2003 | Hodges et al. |
| 2003/0201194 A1 | 10/2003 | Heller et al. |
| 2003/0203498 A1 | 10/2003 | Neel et al. |
| 2004/0079652 A1 | 4/2004 | Vreeke et al. |
| 2004/0120848 A1 | 6/2004 | Teodorczyk |
| 2004/0140209 A1* | 7/2004 | Choi et al. ............... 204/403.01 |
| 2004/0182703 A1 | 9/2004 | Bell et al. |
| 2004/0203137 A1 | 10/2004 | Hodges et al. |
| 2004/0232009 A1* | 11/2004 | Okuda et al. ................. 205/789 |
| 2005/0004439 A1 | 1/2005 | Shin et al. |
| 2006/0108236 A1 | 5/2006 | Kasielke et al. |
| 2006/0134713 A1 | 6/2006 | Rylatt et al. |
| 2006/0200017 A1 | 9/2006 | Monfre et al. |
| 2006/0217602 A1 | 9/2006 | Abul-Haj et al. |
| 2007/0024287 A1 | 2/2007 | Graves et al. |
| 2007/0034529 A1 | 2/2007 | Bard et al. |
| 2007/0074977 A1 | 4/2007 | Guo et al. |
| 2007/0084734 A1* | 4/2007 | Roberts et al. ................ 205/792 |
| 2007/0131565 A1 | 6/2007 | Fujiwara et al. |
| 2007/0154951 A1 | 7/2007 | Kermani |
| 2007/0227912 A1 | 10/2007 | Chatelier et al. |
| 2007/0231914 A1 | 10/2007 | Deng et al. |
| 2007/0235346 A1* | 10/2007 | Popovich et al. .......... 205/777.5 |
| 2008/0093230 A1 | 4/2008 | Diamond et al. |
| 2008/0098802 A1 | 5/2008 | Burke et al. |
| 2008/0105568 A1 | 5/2008 | Wu |
| 2008/0173552 A1 | 7/2008 | Wu et al. |
| 2008/0179197 A1 | 7/2008 | Wu |
| 2008/0199894 A1 | 8/2008 | Galasso |
| 2008/0214910 A1 | 9/2008 | Buck |
| 2008/0274447 A1 | 11/2008 | Mecklenburg |
| 2008/0293082 A1 | 11/2008 | Heller |
| 2009/0000959 A1 | 1/2009 | Feldman et al. |
| 2009/0005666 A1 | 1/2009 | Shin et al. |
| 2009/0017483 A1 | 1/2009 | Yamaoka et al. |
| 2009/0042306 A1 | 2/2009 | Reynolds et al. |
| 2009/0045076 A1 | 2/2009 | Burke et al. |
| 2009/0084687 A1 | 4/2009 | Chatelier et al. |
| 2009/0089010 A1 | 4/2009 | Burke et al. |
| 2009/0101523 A1 | 4/2009 | Deng |
| 2009/0112478 A1 | 4/2009 | Mueller, Jr. et al. |
| 2009/0157344 A1 | 6/2009 | Burke et al. |
| 2009/0292489 A1 | 11/2009 | Burke et al. |
| 2009/0301899 A1 | 12/2009 | Hodges et al. |
| 2010/0006452 A1 | 1/2010 | Hodges et al. |
| 2010/0059391 A1* | 3/2010 | Ying et al. .................... 205/792 |
| 2010/0089775 A1 | 4/2010 | Chen et al. |
| 2010/0173396 A1 | 7/2010 | Miller et al. |
| 2010/0270178 A1 | 10/2010 | Guo et al. |
| 2011/0073493 A1 | 3/2011 | Chatelier et al. |
| 2011/0155585 A1 | 6/2011 | Chatelier et al. |
| 2011/0155589 A1 | 6/2011 | Chatelier et al. |

FOREIGN PATENT DOCUMENTS

| | | |
|---|---|---|
| CN | 1633596 A | 6/2005 |
| CN | 1809746 A | 7/2006 |
| CN | 1975421 A | 6/2007 |
| CN | 101438143 A | 5/2009 |
| CN | 101529236 A | 9/2009 |
| EP | 0735363 A1 | 10/1996 |
| EP | 1 433 322 A1 | 8/2004 |
| EP | 1 688 742 A1 | 8/2006 |
| EP | 1 729 119 A1 | 12/2006 |
| EP | 1839571 A1 | 10/2007 |
| JP | 2000-500571 | 1/2000 |
| JP | 2000-193640 | 7/2000 |
| JP | 2005-526260 | 9/2005 |
| JP | 2006-239062 | 9/2006 |
| JP | 2007-303968 | 11/2007 |
| JP | 2009-294213 | 12/2009 |
| TW | 200745543 A | 12/2007 |
| WO | WO 97/18465 | 5/1997 |
| WO | WO03034055 A1 | 4/2003 |
| WO | 03/069304 A2 | 8/2003 |
| WO | WO 03/097860 A1 | 11/2003 |
| WO | WO 2004/065951 A1 | 8/2004 |
| WO | 2006036833 A2 | 4/2006 |
| WO | WO 2006/119106 A1 | 11/2006 |
| WO | WO 2007/121111 A2 | 10/2007 |
| WO | WO2008/150436 * | 12/2008 |
| WO | WO 2008/150436 A1 | 12/2008 |
| WO | WO-2008150436 | 12/2008 |
| WO | WO-2008150436 A1 | 12/2008 |
| WO | 2009/140343 A1 | 11/2009 |

OTHER PUBLICATIONS

Extended EP Search Report in EP 10252245.5, dated Jul. 7, 2011.
"WaveSense White Paper: Performance of the WaveSense KeyNote Blood Glucose Monitoring System Across 23 Lots of Test Strips", WaveSense, Mar. 2007, XP002640744, URL: http://www.wavesense.info/uploads/pdf/23lotstudyKeyNote.pdf.pdf.
International Search Report and Written Opinion in PCT/US10/62629, dated Feb. 23, 2011.
Australian Examiner's first report for Application No. 2010257395, dated Jun. 28, 2011, 2 pages.
U.S. Appl. No. 12/570,268, Chatelier et al.
U.S. Appl. No. 12/649,594, Chatelier et al.
International Search Report and Written Opinion in PCT/IB2011/002472, dated Dec. 29, 2011 (12 Pages).
International Search Report/Written Opinion for Singapore Application No. 201009143-7; mailed Mar. 29, 2012; 15 pages.
Japanese Office Action for JP 2012-270242; dated Aug. 6, 2013; 2 pages.

(56) References Cited

OTHER PUBLICATIONS

Canadian Office Action for CA 2,723,353; dated Mar. 8, 2013; 3 pages.
Chinese Office Action and Search Report for CN 201010624642.0; dated Nov. 9, 2012 and Nov. 21, 2012; 33 pages.
Japanese Office Action for JP 2012-158824; dated Mar. 12, 2013; 3 pages.
Japanese Office Action for JP 2012-270242; dated Mar. 12, 2013; 3 pages.
Korean Office Action for KR Application No. 1002012-0089149; mailing date Nov. 20, 2012; 5 pages.
Korean Office Action for KR Application No. 10-2010-0135411; dated Dec. 24, 2012; 4 pages.
Korean Office Action from corresponding KR Patent Application No. 10-2010-0135411, dated Jun. 14, 2012 (mailed Jun. 18, 2012, attached pp. 1 through 3.
Chinese Office Action for CN 201010624642.0; dated Oct. 21, 2013; 5 pages.
Japanese Office Action for JP 2012-158824; dated Dec. 10, 2013; 3 pages.
CA Office Action for 2,723,353; dated Oct. 28, 2013; 3 pgs.
CN Office Action and Search Report for Chinese Patent Application No. 201010624642.0; dated May 5, 2014; 18 pages.

\* cited by examiner gal 1342

SYSTEMS, DEVICES, AND METHODS FOR MEASURING WHOLE BLOOD HEMATOCRIT BASED ON INITIAL FILL VELOCITY

FIELD

The present disclosure relates to determining a concentration of an analyte in a sample, and more particularly relates to making a more accurate determination of the concentration based on an initial fill velocity of the sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed. Some of these devices include electrochemical cells, electrochemical sensors, hemoglobin sensors, antioxidant sensors, biosensors, and immunosensors.

One characteristic of blood that can affect analyte detection is the hematocrit. Levels of hematocrit can be vastly different amongst various people. By way of non-limiting example, a person suffering from anemia may have a hematocrit level of approximately 20% while a neonate may have a hematocrit level of approximately 65%. Even samples taken from the same individual over a period of time can have different hematocrit levels. Further, because high hematocrit can also increase the viscosity of blood, and viscosity can in turn affect other parameters associated with analyte detection, accounting for the effect of hematocrit on a sample can be important in making accurate analyte concentration determinations.

One way in which varying levels of hematocrit in a blood sample have been accounted for is by separating the plasma from the blood and then recalculating the concentration of the antigen with respect to the adjusted plasma volume. Separation has been achieved, for example, by performing a centrifugation step. Other ways in which the varying levels of hematocrit in a blood sample have been accounted for include using an average hematocrit in a calculation or measuring a hematocrit in a separate step and then calculating the concentration of the antigen with respect to the plasma value. These methods, however, are believed to be undesirable, at least because they involve unwanted sample handling, take additional time, and lead to substantial errors in the final determinations. Further, temperatures in environments where samples are analyzed can also have a negative impact on the accuracy of analyte concentration determination.

Accordingly, it would be desirable to develop a way to obtain more accurate analyte concentration measurements that account for a wide spectrum of hematocrit levels and temperatures. It would also be desirable to develop a way to determine hematocrit levels quickly.

SUMMARY

Applicants have recognized that it would be desirable to develop a way to obtain more accurate analyte concentration measurements that account for a wide spectrum of hematocrit levels and temperatures with little or none of the attendant issues noted previously. Applicants have also recognized that it would also be desirable to develop a way to determine hematocrit levels quickly. Accordingly, systems, devices, and methods are generally provided for determining a hematocrit value of a blood sample and for determining a concentration of an analyte in a sample. In one exemplary embodiment of a method for determining a hematocrit value of a whole blood sample, the method includes providing a sample of whole blood to a sample analyzing device having a capillary space, measuring an initial fill velocity of the sample in at least a portion of the capillary space, and determining a hematocrit value of the sample from the initial fill velocity. Measuring the initial fill velocity can include applying an electrical potential, measuring an electrical current, and determining an initial current flow. In one embodiment, current measurements are performed approximately every 10 milliseconds for at least approximately 50 milliseconds and an average current based on the current measurements is calculated. In another alternative embodiment, measuring the initial fill velocity can include detecting an optical signal. In one embodiment, measuring an initial fill velocity occurs directly after the sample enters the capillary space. In still another embodiment, measuring an initial fill velocity occurs after the sample crosses into a region of the capillary space of the sample analyzing device where a detection signal is generated. A temperature of the sample can be measured or inferred. The measured or inferred temperature can be used to determine the hematocrit value of the sample. In one exemplary embodiment, the sample analyzing device includes an immunosensor.

In addition to measuring a hematocrit level, the method can also be used to determine a concentration of an analyte in a sample. For example, the method for determining a hematocrit value can include calculating a concentration of the analyte in view of the determined hematocrit value. This can be achieved, for example, by applying an electric potential, measuring an initial current after applying the electric potential, and reversing the electric potential. A change in current over a period of time can be measured following the reversal of the electric potential. The measured change in current over a period of time can also be used to calculate a concentration of the analyte. In one embodiment, a temperature of the sample can either be measured or inferred. In such an embodiment, a measured change in current over a period of time and the temperature of the sample can be used to calculate a concentration of the analyte.

In an exemplary embodiment of a method for determining a concentration of an analyte in a sample, the method includes providing a sample including an analyte to a sample analyzing device having a working and a counter electrode, applying an electric potential between the working and counter electrodes, determining an initial fill velocity of the sample, and calculating a concentration of the analyte in view of the initial fill velocity. In one embodiment, the initial fill velocity can be determined by determining a rate of change in an optical signal. In another embodiment, the initial fill velocity can be determined by determining an initial current flow. The initial current flow can be determined, for example, by performing current measurements approximately every 10 milliseconds for at least approximately 50 milliseconds, and then calculating an average current based on the current measurements. In yet another embodiment, the initial fill velocity can be determined by measuring an initial current after applying the electric potential, determining a level of hematocrit in the sample, and reversing the electric potential between the working and counter electrodes. Further, the concentration of the analyte can be computed based on the determined level of hematocrit.

The method for determining a concentration of an analyte can further include measuring a change in current over a period of time, i.e., the slope m of a current versus time graph, following the reversal of the electric potential. As a result, a concentration of the analyte, $C_O$, can be calculated in view of the change in current over the period of time. For example, the concentration of the analyte can be calculated using the following equation:

$$C_O = -3.5 + 0.866 \exp(y)$$

where $$y = \frac{m}{(1 - 0.01H)^{0.83}}$$

and H is the level of hematocrit. The level of hematocrit H can be determined by using the following equation:

$$H = 97.6 - 1.7658|i_i|$$

where $|i_i|$ is the absolute value of the initial current.

The sample analyzing device can be an immunosensor. The analyte for which the concentration is being analyzed can be C-reactive protein. The analyzed sample can be blood. In one embodiment, the blood includes whole blood. The method can further include measuring a temperature T of the whole blood, or alternatively, measuring an ambient temperature and using it to infer the temperature T of the blood. The method can also further include measuring a change in current over a period of time, i.e., the slope m of a current versus time graph, following the reversal of the electric potential. As a result, a concentration of the analyte, $C_O$, can be calculated in view of the change in current over the period of time. For example, the concentration of the analyte can be calculated using the following equation:

$$C_O = -5.7 + 1.78 \exp(y')$$

where $$y' = \frac{y}{1 + 0.068(T - 25)},$$
$$y = \frac{m}{(1 - 0.01H)^{1.55}},$$

and H is the level of hematocrit. The level of hematocrit H can be determined by the following equation:

$$H = 77.1 - 2.1|i_i| + 0.75T$$

where $|i_i|$ is the absolute value of the initial current.

In one exemplary embodiment of an electrochemical system, the system includes an immunosensor having lower and upper electrodes, a meter configured to apply a potential between the lower and upper electrodes of the immunosensor, and a control unit configured to measure an initial fill velocity of a sample introduced into the immunosensor. The control unit is further configured to use the initial fill velocity to calculate at least one of a value of hematocrit of the sample when the sample includes blood and a concentration of an analyte in the sample. The system can also include a heating element that is configured to heat at least a portion of the immunosensor.

The immunosensor can include a first liquid reagent, a second liquid reagent, and magnetic beads conjugated to an antigen. In one embodiment, the first liquid reagent can include an antibody conjugated to an enzyme in a buffer. The first liquid reagent can be striped on the lower electrode and can be dried. The second liquid reagent can include ferricyanide, a substrate for the enzyme, and a mediator in a dilute acid solution. The second liquid reagent can be striped on the lower electrode and can be dried. The magnetic beads, on the other hand, can be striped on the upper electrode and dried.

The immunosensor can also include a plurality of chambers, a separator, a vent, and one or more sealing components. The separator can be disposed between the lower and the upper electrodes. The plurality of chambers can include a reaction chamber, a detection chamber, and a fill chamber. The reaction chamber can be formed in the separator and can have the first reagent and the magnetic beads conjugated to the antigen disposed therein. The detection chamber can also be formed in the separator and can have the second reagent disposed therein. The fill chamber can be formed at least partially in the separator and one of the lower and upper electrodes, can be spaced a distance apart from the detection chamber, and can overlap at least a portion of the reaction chamber. The vent can be formed at least partially in each of the separator, the lower electrode, and the upper electrode, can be spaced a distance apart from the reaction chamber, and can overlap at least a portion of the detection chamber. In one embodiment, the one or more sealing components can be a first sealing component and a second sealing component. The first sealing component can have an incorporated anticoagulant coupled to one of the lower and upper electrodes, can be disposed over the vent, and can be configured to both form a wall of the fill chamber and seal the vent. The second sealing component can be coupled to the other of the lower and upper electrodes, can be disposed over the vent, and can be configured to seal the vent. In one embodiment, the first sealing component includes a hydrophilic adhesive tape.

In one embodiment, the control unit of the electrochemical system can include an optical signal detector that is configured to measure a rate of change in an optical signal to measure the initial fill velocity of the sample. In another embodiment, the control unit can include a current flow detector configured to measure an initial current flow to measure the initial fill velocity of the sample. In still another embodiment, the control unit can be configured to measure the initial fill velocity of the sample directly after the sample enters a capillary space of the immunosensor. In yet another embodiment, the control unit can be configured to measure the initial fill velocity after the sample crosses into a region of a capillary space of the immunosensor where a detection signal is generated. At least one of the control unit, the immunosensor, and the meter can be configured to measure a temperature of the sample or infer a temperature of the sample.

The analyte for which the system calculates the concentration can be C-reactive protein. The sample introduced into the immunosensor can be blood. In one embodiment, the blood includes whole blood.

The sample analyzing device can also be a number of other analyzing devices, including, by way of non-limiting example, electrochemical cells, electrochemical sensors, glucose sensors, glucose meters, hemoglobin sensors, antioxidant sensors, and biosensors. In one embodiment, the sample analyzing device includes a glucose sensor. The glucose sensor can include an electrochemical cell having a working electrode and a counter or counter/reference electrode. The working electrode and the counter or counter/reference electrode can be spaced apart by approximately 500 micrometers or less. In one embodiment, a spacing between the electrodes is in the range of about 80 micrometers to about 200 micrometers. The spacing can be determined in order to achieve a desired result, for example, substantially achieving a steady state current in a desirable time. In one embodiment, a spacing between the electrodes is selected such that the reaction products from a counter electrode arrive at a working electrode.

The working and counter or counter/reference electrode can have a variety of configurations. For example, the electrodes can be facing each other, they can be substantially opposed to each other, or they can have a side-by-side configuration in which the electrodes are positioned approximately in the same plane. The electrodes can have substantially the same corresponding area. The electrodes can also be planar. In one embodiment, the electrochemical cell includes a working electrode, a counter electrode, and a separate reference electrode. In another embodiment, the electrochemical cell can have two electrode pairs. The electrode pairs can include any combination of working, counter, counter/reference, and separate reference electrodes, but in one exemplary embodiment, each pair includes a working electrode and a counter or counter/reference electrode. In still another embodiment, the electrochemical cell can have an effective cell volume of about 1.5 microliters or less. The electrochemical cell can alternatively be hollow.

A potential can be applied to the electrodes of the cells by a number of different mechanisms, including, by way of non-limiting example, a meter. The magnitude of the potential can depend on a number of different factors, including, by way of non-limiting example, the desired reaction of the sample within the cell. In one embodiment, the magnitude of the potential can be selected such that electro-oxidation of a reduced form or electro-reduction of an oxidized form of a sample is substantially diffusion controlled.

Samples can enter the cell by way of capillary action. A control unit can be used to determine an initial velocity of the sample entering the cell. In one embodiment, the control unit can include an optical signal detector that is configured to measure a rate of change in an optical signal to measure the initial fill velocity of the sample. In another embodiment, the control unit can include a current flow detector configured to measure an initial current flow to measure the initial fill velocity of the sample. In still another embodiment, the control unit can be configured to measure the initial fill velocity of the sample directly after the sample enters a capillary space of the electrochemical cell. In yet another embodiment, the control unit can be configured to measure the initial fill velocity after the sample crosses into a region of a capillary space of the electrochemical where a detection signal is generated. At least one of the control unit, the electrochemical cell, and the meter can be configured to measure a temperature of the sample or infer a temperature of the sample.

One exemplary embodiment of a method for measuring an antigen in a blood sample can include providing an immunosensor having two electrodes and a meter configured to apply a potential between the two electrodes of the immunosensor. The method can further include introducing a blood sample including an antigen into the immunosensor, applying an electric potential between the two electrodes, determining an initial fill velocity of the blood sample, and calculating a concentration of the antigen in view of the initial fill velocity. In an alternative embodiment, the method can be set-up to only measure a hematocrit level of the blood, or to measure both a hematocrit level of the blood and a concentration of the antigen in the blood. The immunosensor can further include a reaction chamber and a detection chamber formed in a separator disposed between the two electrodes, a fill chamber at least partially formed in the separator and one of the two electrodes, and a vent at least partially formed in the separator and the two electrodes. The fill chamber can be spaced a distance apart from the detection chamber and can overlap at least a portion of the reaction chamber. The vent can be spaced a distance apart from the reaction chamber and can overlap at least a portion of the detection chamber. The antigen of the blood sample can be C-reactive protein. The method can further include measuring a temperature of the blood sample, or alternatively inferring a temperature of the blood sample, and then measuring a change in current over a period of time after reversing the electric potential. As a result, a concentration of the antigen can be calculated in view of the change in current over the period of time and the measured or inferred temperature.

The method for measuring a blood sample can further include providing an antibody-enzyme conjugate in a first buffer and magnetic beads linked to an antigen in a second buffer in the reaction chamber. Ferricyanide, glucose, and a mediator in a dilute acid can be provided in the detection chamber. A first seal can be provided over a first side of the vent that forms a wall of the fill chamber and a second seal can be provided over a second side of the vent. At least a portion of the blood sample that is introduced into the immunosensor moves from the fill chamber to the reaction chamber when it is introduced into the immunosensor.

The method can further include opening the vent after a pre-determined time by piercing at least one of the seals. Piercing at least one of the seals allows portions of the blood sample containing the antibody-enzyme conjugate that are not bound to the magnetic beads to move to the detection chamber. Still further, the method can include catalyzing oxidation of the glucose in the detection chamber, which can result in the formation of ferrocyanide. A current can be electrochemically detected from the ferrocyanide, and a concentration of the antigen in the blood sample can be calculated in view of the signal detected.

In one embodiment, determining an initial fill velocity can include measuring an initial current after applying the electric potential, determining a level of hematocrit in the sample, and reversing the electric potential between the working and counter electrodes. Accordingly, the concentration of the analyte can be computer based on the determined level of hematocrit. The method can further include measuring a change in current over a period of time following reversing the electric potential. Accordingly, the concentration of the analyte can be calculated in view of the change in current over the period of time. In another embodiment, determining an initial fill velocity can include determining a rate of change in an optical signal to determine the initial fill velocity. In still another embodiment, determining an initial fill velocity can include determining an initial current flow to determine the initial fill velocity. The initial fill velocity can be determined directly after the blood sample enters a capillary space of the immunosensor. Alternatively, the initial fill velocity can be determined after the blood sample crosses into a region of a capillary space of the immunosensor where a detection signal is generated.

BRIEF DESCRIPTION OF DRAWINGS

This invention will be more fully understood from the following detailed description taken in conjunction with the accompanying drawings, in which.

DETAILED DESCRIPTION

Figure 1:
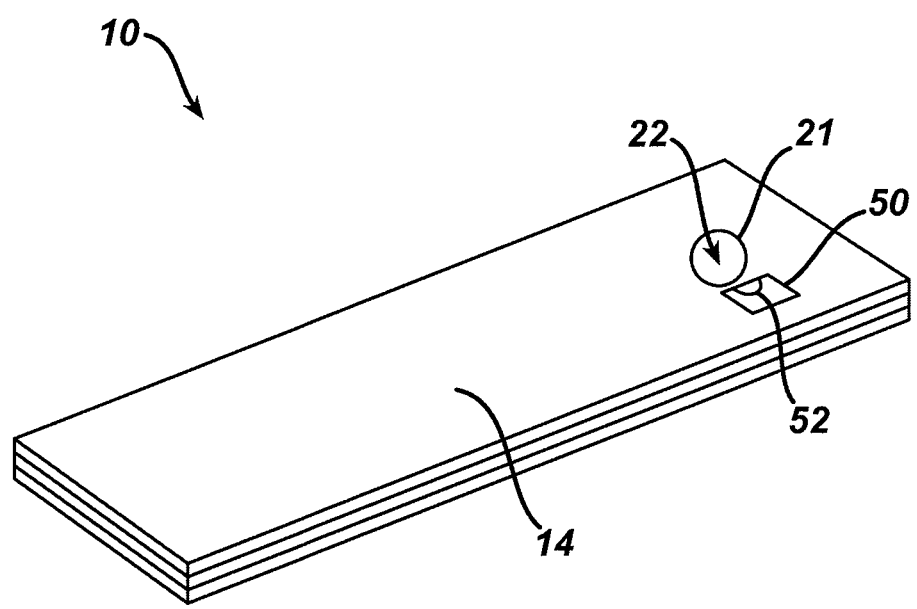
FIG. 1 illustrates a perspective view of one exemplary embodiment of an immunosensor and a control unit having an optical detector for calculating an initial fill velocity in accordance with the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, while some embodiments discuss determining a value of hematocrit of a sample while other embodiments discuss determining a concentration of an analyte in a sample, one skilled in the art will recognize that the teachings associated with each type of embodiment are equally applicable to the other type of embodiment. That is, embodiments directed to determining hematocrit values can also be used to determine a concentration of an analyte in a sample, and embodiments directed to determining a concentration of an analyte can be used solely to determine a hematocrit value of a sample. Further, embodiments can both be used to determine a hematocrit value of a sample and determine a concentration of an analyte in a sample.

The methods for determining a value of hematocrit in a sample and determining a concentration of an analyte in a sample disclosed herein can be used with any sample analyzing device and/or system. The devices can have a capillary space. The devices can include at least one working electrode and one counter electrode between which an electric potential can be applied. The sample analyzing device can generally be associated with a component for applying the electric potential between the electrodes, such as a meter. The sample analyzing device can also be associated with one or more components that are capable of measuring an initial fill velocity of a sample when it is introduced to the device. Such components can also be capable of calculating a concentration of an analyte in the sample in view of the initial fill velocity. Such components are generally referred to herein as control units. Further, the terms analyte, antigen, and antibodies are used interchangeably within, and thus, use of one term is equally applicable to all three terms, unless otherwise indicated or reasonably known by one skilled in the art.

In one exemplary embodiment of a method for determining a hematocrit value of a whole blood sample, a sample of whole blood is provided to a sample analyzing device having a capillary space. An initial fill velocity of the sample in at least a portion of the capillary is measured. A hematocrit value of the sample is then determined from the initial fill velocity. A concentration of an analyte or antigen in the sample can be determined in view of the determined value of hematocrit. Using the initial fill velocity to calculate the hematocrit value can allow for improved accuracy. Methods for determining a hematocrit value can also account for the effects of temperature, as discussed in greater detail below. Further, by measuring for only a value of hematocrit, without reference to an associate analyte concentration, determinations can be achieved almost instantaneously, often in less than a second. For example, hematocrit levels of a drop of blood can be determined in less than a second merely by dropping the blood onto a sensor strip of a sample analyzing device. Once the blood is disposed on the strip, a digital readout of the hematocrit level can be provided almost instantaneously. The result is quick and accurate determinations of hematocrit levels, which are useful for a variety of medical assessments, for example, making assessments related to conditions such as anemia.

In another exemplary embodiment of a method for determining a concentration of an analyte in a sample, a sample is provided to a sample analyzing device that has a working electrode and a counter electrode. An electric potential can be applied between the working and counter electrodes of the sample analyzing device and an initial fill velocity of the sample into a capillary space of the sample analyzing device can be determined. A concentration of the analyte in the sample can be calculated in view of the determined initial fill velocity. By calculating the concentration in view of the initial fill velocity, errors, such as those that can result from varying hematocrit levels across samples, can be accounted for, thereby leading to more accurate determinations of the concentrations of the analytes in the samples. Methods can also account for the effects of temperature, as discussed in greater detail below. In an alternative embodiment for detecting a concentration of an analyte in a sample, errors are corrected for based on a determined fill time rather than a determined initial fill velocity. One example of such a device is disclosed in a co-pending patent application entitled "Systems, Devices, and Methods for Improving Accuracy of Biosensors Using Fill Time," of Ronald C. Chatelier and Alastair M. Hodges, filed concurrently with the present application on Dec. 30, 2009, and which is hereby incorporated by reference in its entirety. In an alternative embodiment, a concentration of an antigen in a plasma phase and an estimate of a level of hematocrit level can be determined.

An initial fill velocity can be used in a variety of ways to determine a concentration of an analyte. For example, if the sample includes whole blood and a temperature of the location where the sample is being analyzed in the sample analyzing device is known, the initial fill velocity can be linked to the determined hematocrit level. A temperature of the sample may be known, for example, if a chamber of a sample analyzing device is preheated to a desired temperature. If a temperature is not known, calculations can still be performed that allow for the temperature to be measured or inferred during reactions. In such an instance, the temperature and hematocrit levels can both be accounted for in order to provide more accurate analyte concentration determinations. Further, an initial fill velocity can likewise be used in a variety of ways to determine a hematocrit level of a blood sample.

There are a variety of ways to determine the initial fill velocity associated with the sample entering the sample analyzing device. Determining the initial fill velocity, in turn, can allow a viscosity of a liquid to be estimated. Estimating a viscosity of a liquid can assist in making more accurate concentration determinations. In one exemplary embodiment, as shown in FIG. 1, an immunosensor 10 includes a control unit 50 having an optical detector 52 generally located near an entry port 21 to a fill chamber 22 of the immunosensor 10. The optical detector 52 can have any shape or size, and can be located, for example, on top of the immunosensor 10 or just inside of the entry port 21 of the immunosensor 10. In the illustrated embodiment, the optical sensor is coupled to a top plate 14 of the immunosensor 10, adjacent the entry port 21. The optical sensor 52 can include an optical signal that changes when a sample passes by the sensor 52. Thus, as a sample is provided to the immunosensor 10, a rate of change of the optical signal can be detected, which in turn can be used to estimate the initial fill velocity. The rate of change can be measured in at least a portion of a capillary space of the immunosensor 10. The initial fill velocity can then be used to calculate a number of different parameters. By way of non-limiting example, the initial fill velocity can be used to calculate a concentration of an antigen in a sample or a hematocrit level of a whole blood sample.

In another exemplary embodiment, an electrochemical detection system can be used to measure a magnitude of an initial current flow. The magnitude can be measured as soon as the sample enters a capillary space of the sample analyzing device. Capillary space can be located, for example, prior to an initial entrance into a fill chamber, between a fill chamber and a reaction chamber, and/or between a reaction chamber and a detection chamber. In one exemplary embodiment, the initial current flow is determined between the fill chamber and the reaction chamber. In another exemplary embodiment, the initial current flow is measured when the sample first crosses into a region of capillary space of the sample analyzing device where a detection signal can be generated, such as a detection chamber.

A number of different techniques can be used to measure the current flow. For example, a desired number of measurements can be taken over a desired length of time. In one exemplary embodiment, a measurement is made approximately in the range of about every 1 millisecond to about every 25 milliseconds over a period of approximately at least about 10 milliseconds to about 300 milliseconds. In another embodiment, a measurement is made approximately every 10 milliseconds over a period of approximately at least 50 milliseconds. A single measurement can also be taken, but typically more accurate results for the initial velocity can be obtained by making multiple measurements over a short period of time. One skilled in the art will recognize that there are a variety of other ways by which the initial current and/or initial velocity of the sample can be determined, some of which are disclosed in greater detail below.

Figure 2:
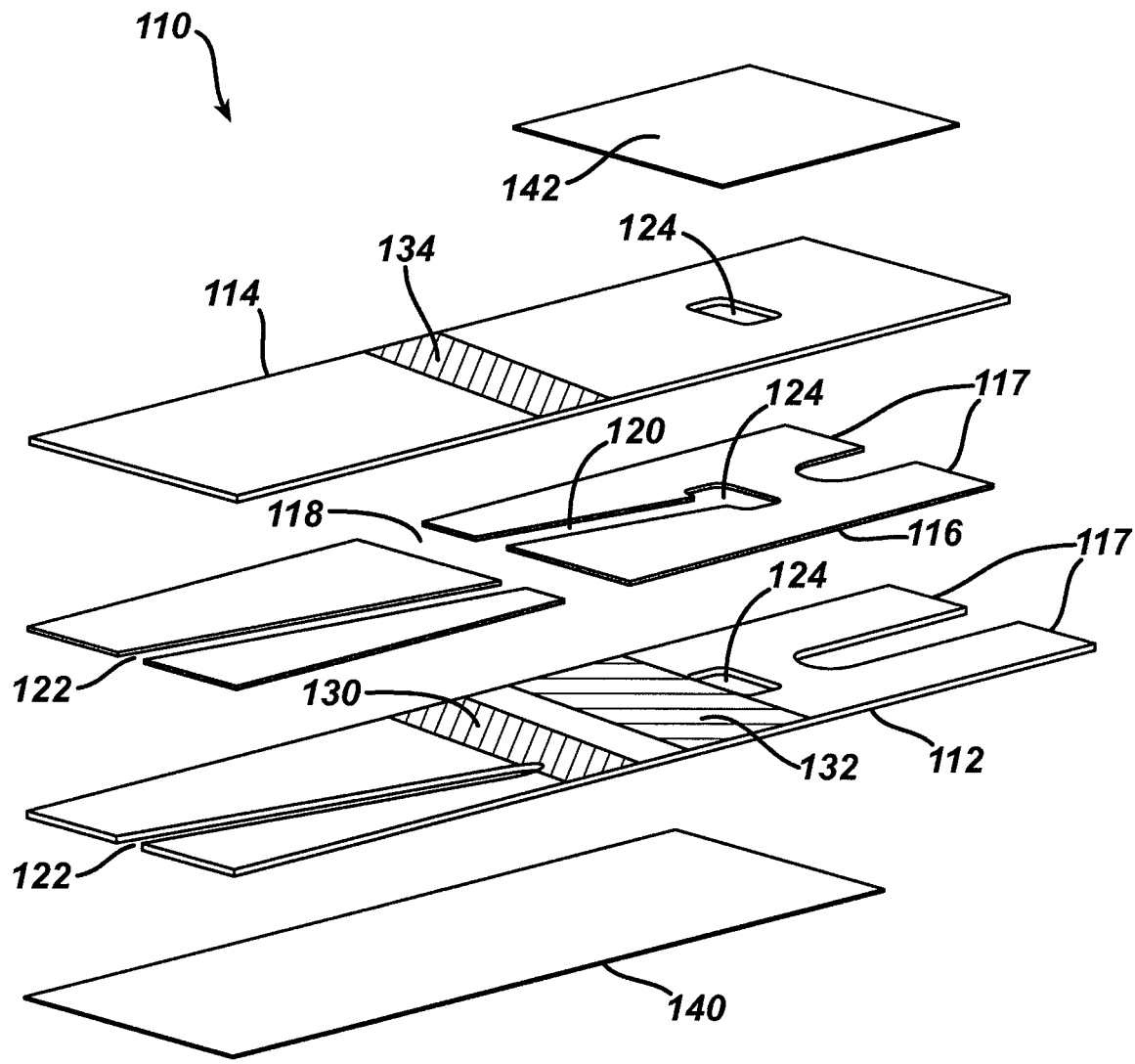
FIG. 2 illustrates an exploded view of another exemplary embodiment of an immunosensor in accordance with the present invention, wherein the immunosensor is configured for use with a control unit having an electrochemical detection system for calculating an initial fill velocity.

Another exemplary embodiment of a sample analyzing device for use in conjunction with at least some of the methods disclosed herein, an immunosensor 110, is illustrated in FIG. 2 and is described in U.S. patent application Ser. No. 12/570,268 of Chatelier et al., entitled "Adhesive Compositions for Use in an Immunosensor" and filed on Sep. 30, 2009, the contents of which is hereby incorporated by reference in its entirety. A plurality of chambers can be formed within the immunosensor, including a fill chamber, by which a sample can be introduced into the immunosensor, a reaction chamber, by which a sample can be reacted with one or more desired materials, and a detection chamber, by which a concentration of a particular component of the sample can be determined. These chambers can be formed in at least a portion of a lower electrode, an upper electrode, and a separator of the immunosensor. The immunosensor can also include a vent hole to allow air to enter and escape the immunosensor as desired, and first and second sealing components to selectively seal first and second sides of the vent hole. The first sealing component can also form a wall of the fill chamber.

As illustrated, the immunosensor 110 includes a lower electrode 112 having two liquid reagents 130, 132 striped onto it. The lower electrode 112 can be formed using any number of techniques used to form electrodes, but in one embodiment a polyethylene terephthalate (PET) sheet that is filled with barium sulphate is sputter-coated with a suitable conductor, such as, for example, gold. Other non-limiting example of forming an electrode are disclosed in U.S. Pat. No. 6,521,110 of Hodges et al., entitled "Electrochemical Cell" and filed on Nov. 10, 2000, the contents of which is hereby incorporated by reference in its entirety.

Likewise, the liquid reagents 130, 132 may have a number of different compositions. In one embodiment, the first liquid reagent 130 includes an antibody conjugated to an enzyme, such as, for example, GDH-PQQ, in a buffer that contains sucrose, as well as a poloxamer, such as, for example, Pluronics® block copolymers, an anticoagulant, such as citraconate, and calcium ions. In one embodiment, the second liquid reagent 132 includes a mixture of ferricyanide, glucose, and a second mediator, such as phenazine ethosulfate, in an acidic buffer, such as a dilute citraconic acid solution. The first and second liquid reagents 130, 132 can be dried onto the lower electrode 112. A number of techniques can be used to dry the reagents 130, 132, but in one embodiment, following the striping of the reagents 130, 132 on the lower electrode 112, one or more infrared dryers can be applied to the reagents 130, 132. One or more air dryers can also be used, for example, subsequent to the infrared dryers. References to a first reagent and a first liquid reagent and a second reagent and a second liquid reagent herein are used interchangeably and are not necessarily an indication that the reagents are in their liquid or dried form at a given time for a particular embodiment. Further, some of the components associated with the first and second liquid reagents can be used interchangeably and/or in both the first and second liquid reagents as desired. By way of non-limiting example, an anticoagulant can be associated with either or both of the first liquid reagent 130 and the second liquid reagent 132.

A line can be formed in the sputter-coated gold between the reagents 130, 132 such that an edge of one of the reagents 130, 132 is very close to, or touches, the line. In the illustrated embodiment, the line is formed such that an edge of the reagent 132 touches the line at vent 124. The line can be applied using laser ablation or with a sharp metal edge. In one exemplary embodiment, the line can be applied before the reagents 130, 132 are striped on the electrode. The line can be designed to electrically insulate the section of the lower electrode 112 under the detection chamber from the section that will be under the reaction chamber. This can provide a better definition of an area of the working electrode during the electrochemical assay.

The immunosensor 110 can also include an upper electrode 114 having one or more magnetic beads 134 containing surface-bound antigens thereon. The antigens can be configured to react with the antibody disposed on the lower electrode 112 and the sample within a reaction chamber 118, as described in further detail below. One skilled in the art will recognize that the components disposed on the lower electrode 112 and on the upper electrode 114 can be interchangeable. Thus, the lower electrode 112 can include one or more magnetic beads 134 and the upper electrode 114 can include two liquid reagents 130, 132 striped onto it. Further, although in the illustrated embodiment the length of the electrode 112 forms the length of the entire body of the immunosensor 110, in other embodiments the electrode can be only a portion of a layer of an immunosensor that serves as the lower or upper electrode or multiple electrodes can be disposed on a single layer of an immunosensor. Further, because potential applied to the immunosensor can be flipped and/or alternated, each of the lower and upper electrodes can serve as the working electrode and the counter or counter/reference electrode at different stages. For ease of description purposes, in the present application the lower electrode is considered the working electrode and the upper electrode the counter or counter/reference electrode.

A separator 116 disposed between the lower and upper electrodes 112, 114 can have a variety of shapes and sizes, but it generally is configured to desirably engage the lower and upper electrodes 112, 114 to form the immunosensor 110. In one exemplary embodiment, the separator 116 includes adhesive properties on both sides. The separator 116 can further include a release liner on each side of the two sides of the separator 116. The separator 116 can be cut in a manner that forms at least two cavities. A first cavity can be formed to serve as a reaction chamber 118 and a second cavity can be formed to serve as a detection chamber 120. In one embodiment, the separator 116 can be kiss-cut such that the reaction chamber 118 is aligned with the electrodes 112, 114 to allow an antigen-antibody reaction therein while the detection chamber 120 is aligned with the electrodes 112, 114 to allow for the electrochemical determination of ferrocyanide therein.

In one embodiment, the separator 116 can be placed on the lower electrode 112 in a manner that allows the magnetic beads 134 of the upper electrode 114 and the first reagent 130 of the lower electrode 112 to be at least partially disposed in the reaction chamber 118 and the ferricyanide-glucose combination of the second reagent 132 of the lower electrode 112 to be at least partially disposed in the detection chamber 120. It can be advantageous to include an anticoagulant in each of the first and second liquid reagents 130, 132 so that an anticoagulant is associated with each of the reaction and detection chambers 118, 120. In some embodiments the combination of one of the upper and lower electrodes 112, 114 and the separator 116 can be laminated together to form a bi-laminate, while in other embodiments the combination of each of the lower electrode 112, the upper electrode 114, and the separator 116 can be laminated together to form a tri-laminate. Alternatively, additional layers may also be added.

A fill chamber 122 can be formed by punching a hole into one of the lower and upper electrodes 112, 114 and the separator 116. In the illustrated embodiment, the fill chamber is formed by punching a hole in the lower electrode 112 and the separator 116 such that the hole in the lower electrode 112 overlaps the reaction chamber 118. As shown, the fill chamber 122 can be a distance apart from the detection chamber 120. Such a configuration allows a sample to enter the immunosensor 110 through the fill chamber 122 and flow into the reaction chamber 118 to be reacted, for example with the first liquid reagent 130 that includes the antibody conjugated to an enzyme in a buffer on the first electrode 112 and the magnetic beads 134 striped on the upper electrode 114, without entering the detection chamber 120. Entry of a sample into the fill chamber 122 can occur by way of capillary action, and as such, at least one of the fill chamber 122, the reaction chamber 118, and a location therebetween can be considered a capillary space. Once the sample has been reacted, it can then flow into the detection chamber 120 for interaction with the second liquid reagent 132, for example, the mixture of ferricyanide, glucose, and the second mediator in an acidic buffer.

A vent 124 can be formed by punching a hole through each of the two electrodes 112, 114 and the separator 116 such that the vent 124 extends through the entirety of the immunosensor 110. The hole can be formed in a suitable manner such as, for example, drilled or punched in a number of different locations, but in one exemplary embodiment it can overlap a region of the detection chamber 120 that is spaced apart from the reaction chamber 118.

The vent 124 can be sealed in a number of different manners. In the illustrated embodiment, a first sealing component 140 is located on the lower electrode 112 to seal a first side of the vent 124 and a second sealing component 142 is located on the upper electrode 114 to seal a second side of the vent 124. The sealing components can be made of and/or include any number of materials. By way of non-limiting example, either or both of the sealing components can be hydrophilic adhesive tape or Scotch® tape. Adhesive sides of the sealing components can face the immunosensor 110. As shown, not only can the first sealing component 140 form a seal for the vent 124, but it can also form a wall for the fill chamber 122 so that the sample can be contained therein. Properties incorporated onto the adhesive side of the first sealing component 140 can be associated with the fill chamber 122. For example, if the first sealing component 140 includes properties making it hydrophilic and/or water soluble, the fill chamber can remain well-wet when a sample is disposed therein. Further, the sealing components 140, 142 can be selectively associated and disassociated with the immunosensor 110 to provide venting and/or sealing for the immunosensor 110 and the components disposed therein as desired.

Adhesives can generally be used in the construction of the immunosensor. Non-limiting examples of ways in which adhesives can be incorporated into immunosensors and other sample analyzing devices of the present disclosure can be found in U.S. patent application Ser. No. 12/570,268 of Chatelier et al., entitled "Adhesive Compositions for Use in an Immunosensor" and filed on Sep. 30, 2009, the contents of which was already incorporated by reference in its entirety.

While the present disclosure discusses a variety of different embodiments related to immunosensors, other embodiments of immunosensors can also be used with the methods of the present disclosure. Non-limiting examples of such embodiments include those described in U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. patent application Ser. No. 12/563,091, which claims priority to each of U.S. Patent Application Publication Nos. 2003/0180814 and 2004/0203137, each of which is hereby incorporated by reference in its entirety.

In one embodiment, the immunosensor 110 can be configured to be placed into a meter that is configured to apply a potential to the electrodes 112, 114 and measure a current that results from the application of the potential. In one embodiment, the immunosensor includes one or more tabs 117 for engaging a meter. Other features can also be used to engage the immunosensor 110 with a meter. The meter can include a number of different features. For example, the meter can include a magnet that is configured to maintain certain components of the immunosensor 110 in one chamber while other components flow to the other. In one exemplary embodiment, the magnet of the meter is located such that, upon placing the immunosensor 110 in the meter, the magnet is disposed below the reaction chamber 118. This can allow the magnet to assist in holding back any magnetic beads 134, and more particularly any antibody-enzyme conjugate that is bound to the beads 134, from flowing into the detection chamber 120.

An alternate feature of the meter includes a heating element. A heating element can help speed up the reaction rate and help the sample flow through the immunosensor 110 in a desired manner by reducing the viscosity. A heating element can also allow one or more chambers and/or a sample disposed therein to be heated to a predetermined temperature. Heating to a predetermined temperature can help provide accuracy, for example, by diminishing or removing the effects of temperature change as reactions occur.

Further, a piercing instrument can also be associated with the meter. The piercing instrument can be configured to pierce at least one of the first and second sealing components at a desired time so that air can flow out of the vent hole and liquid can flow from the reaction chamber into the detection chamber.

The immunosensor 110 can also be configured to be associated with a control unit. The control unit can be configured to perform a variety of functions. In one exemplary embodiment, the control unit is capable of measuring an initial fill velocity of a sample when it is introduced to the device. In another embodiment, the control unit is configured to determine a hematocrit value of a blood sample. In yet another embodiment, the control unit is configured to calculate a concentration of an analyte in the sample in view of the initial fill velocity. In fact, the control unit can include a number of different features, depending, at least in part, on the functionality desired and the method by which the system is designed to measure the initial fill velocity.

By way of non-limiting example, if the system is designed to measure an initial fill velocity optically, the control unit can include an optical signal detector. The optical signal detector can measure an initial fill velocity based on a rate of change in an optical signal sensed by the detector. Alternatively, if the system is designed to measure an initial fill velocity based on current flow, the control unit can include a current flow detector. The current flow detector can measure an initial fill velocity based on a change in current that occurs as a result of the sample entering the immunosensor. The timing of this change can occur in a number of different manners, but in one exemplary embodiment, the current is measured after the sample crosses into a region of a capillary space of the immunosensor where a detection signal is generated, for example, when the sample crosses from the reaction chamber into the detection chamber. In another embodiment, the current is measured directly after the sample enters a capillary space of the immunosensor, for example, when the sample enters the reaction chamber.

The control unit can also measure other aspects of the system. By way of non-limiting example, the control unit can be configured to measure a temperature of one or more chambers of the immunosensor. It can also be configured to measure a temperature of the sample, for instance directly or by measuring an ambient temperature and using it to infer the temperature of the sample, a color of the sample, or a variety of other characteristics and/or properties of the sample and/or the system. By way of further non-limiting example, the control unit can be configured to communicate the results of the initial fill velocity determination, the results of the hematocrit value determination, and/or the results of the analyte concentration determination, to outside equipment. This can be accomplished in any number of ways. In one embodiment, the control unit can be hardwired to a microprocessor and/or a display device. In another embodiment, the control unit can be configured to wirelessly transmit data from the control unit to a microprocessor and/or a display device.

Other components of the system can also be configured to make such measurements. For example, the immunosensor or the meter can be configured to measure a temperature of one or more chambers of the immunosensor, measure or infer the temperature of a sample, or measure, determine, or infer a variety of other characteristics and/or properties of the sample and/or the system. Still further, one skilled in the art will recognize that these features of a control unit can be interchanged and selectively combined in a single control unit. For example, a control unit can both determine an initial fill velocity and measure a temperature of a chamber. In other embodiments, multiple control units can be used together to perform various functions, based at least in part on the configurations of the various control units and the desired functions to be performed.

Other types of sample analyzing devices can be used in conjunction with at least some of the systems and methods disclosed herein. These devices can include, by way of non-limiting example, electrochemical cells, electrochemical sensors, glucose sensors, glucose meters, hemoglobin sensors, antioxidant sensors, and biosensors. In one embodiment, the sample analyzing device includes a glucose sensor. The glucose sensor can include an electrochemical cell, such as the cell illustrated in FIGS. 3 and 4. The cell can include a thin strip membrane 201 having upper and lower surfaces 202, 203, and can also include a cell zone 204 defined between a working electrode 206 disposed on the lower surface 203 and a counter/reference electrode 205 disposed on the upper surface 202. The membrane thickness can be selected to achieve a desired result, such as having the reaction products from a counter electrode arrive at a working electrode. For instance, the membrane thickness can be selected so that the electrodes are separated by a distance t, which can be sufficiently close such that the products of electrochemical reaction at the counter electrode can migrate to the working electrode during the time of the test and a steady state diffusion profile can be substantially achieved. Typically t can be less than approximately 500 micrometers, alternatively in the range of about 10 micrometers to about 400 micrometers, and more particularly in the range of about 80 micrometers to about 200 micrometers. In one embodiment, a spacing between the electrodes can be selected such that the reaction products from a counter electrode arrive at a working electrode.

The electrodes can also have a variety of configurations. For instance, the electrodes can be planar. Further, while in the illustrated embodiment the electrodes 205, 206 are facing each other and are substantially opposed, in other embodiments the electrodes can just be facing each other, they can be substantially opposed to each other, or they can have a side-by-side configuration in which the electrodes are positioned approximately in the same plane. Examples of different electrode configurations can be found at least in U.S. Pat. No. 7,431,820 of Hodges, entitled "Electrochemical Cell," and filed on Oct. 14, 2003, the contents of which is hereby incorporated by reference in its entirety.

A sample deposition or "target" area 207 can be defined on the upper surface 202 of the membrane 201 and can be spaced at a distance greater than the membrane thickness from the cell zone 204. The membrane 201 can have a diffusion zone 208 that can extend between the target area 207 and the cell zone 204. A suitable reagent can include a redox mediator M, an enzyme E, and a pH buffer B, each of which can be contained within the cell zone 204 of the membrane and/or between the cell zone 204 and the target area 207. The reagent can also include stabilizers and the like.

In use of the sensor, a drop of blood can be placed on the target zone 207 and the blood components can wick towards the cell zone 204. The initial velocity at which the blood covers the target zone 207 can depend at least on the hematocrit.

Figure 3:
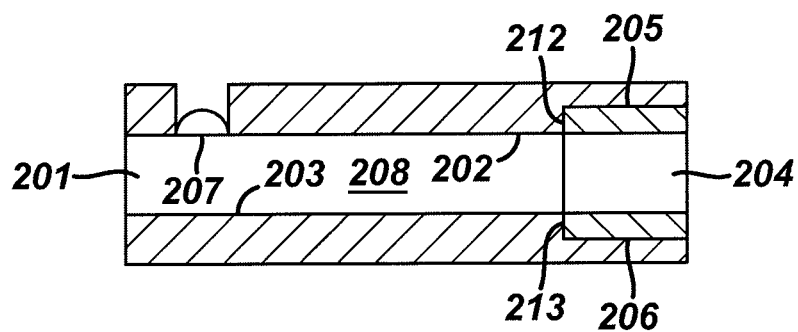
FIG. 3 illustrates a side elevation schematic drawing (not to scale) of an exemplary embodiment of an electrochemical cell in accordance with the present invention.
Figure 4:
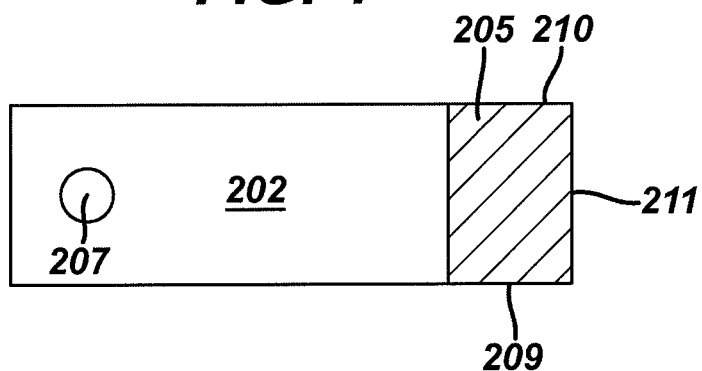
FIG. 4 illustrates a plan view, from above, of the electrochemical cell of FIG. 3.

Each of electrodes 205, 206 can have a predefined area. In the embodiments of FIGS. 3 and 4 the cell zone 204 can defined by edges 209, 210, 211 of the membrane, which can correspond with edges of the electrodes 205, 206 and by leading (with respect to the target area 207) edges 212, 213 of the electrodes. In the present example the electrodes can be about 600 angstrom thick and can be from about 1 mm to about 5 mm wide, although a variety of other dimensions and parameters can be used without departing from the scope of the present invention.

Alternatively, both sides of the membrane can be covered with the exception of the target area 207 by laminating layers which can serve to prevent evaporation of water from the sample and to provide mechanical robustness to the apparatus. Evaporation of water is believed to be undesirable as it concentrates the sample, allows the electrodes to dry out, and allows the solution to cool, affecting the diffusion coefficient and slowing the enzyme kinetics, although diffusion coefficient can be estimated as above.

Figure 5:
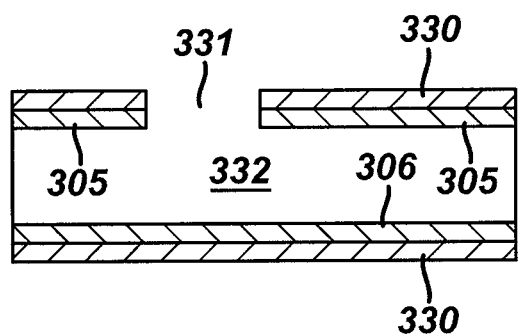
FIG. 5 illustrates a schematic drawing (not to scale), in cross-section, of an exemplary embodiment of a hollow electrochemical cell in accordance with the present invention.

In an alternative embodiment, illustrated in FIG. 5, a hollow electrochemical cell for use with the systems and methods disclosed herein is provided. The electrodes 305, 306 can be supported by spaced apart polymer walls 330 to define a hollow cell. An opening 331 can be provided on one side of the cell whereby a sample can be admitted into the cavity 332. In this embodiment, a membrane is not used, although in some embodiments a membrane can be included. The electrodes can have a variety of configurations, at least as discussed above. By way of non-limiting example, the electrodes can be spaced apart by less than about 500 micrometers, preferably in the range of about 10 micrometers or about 20 micrometers to about 400 micrometers, and more preferably in a range of about 100 micrometers to about 200 micrometers. The effective cell volume can be about 1.5 microliters or less.

The electrochemical cells of FIGS. 3-5 can be used in conjunction with the meters, control units, and other components and steps of the devices, systems, and methods disclosed herein. Further disclosures related to the electrochemical cells of FIGS. 3-5 are found in U.S. Pat. No. 6,284,125 of Hodges et al., entitled "Electrochemical cell" and filed on Apr. 17, 1998, the contents of which is hereby incorporated by reference in its entirety. For example, electrochemical cells used in conjunction with the present disclosures can have two electrode pairs. The electrode pairs can include any combination of working, counter, counter/reference, and separate reference electrodes.

EXAMPLE 1

The use of an electrochemical system to measure an initial fill velocity based on measuring current flow is demonstrated by the following example. In the following example, the system included a sample analyzing device, in particular the immunosensor 110 of FIG. 2, a meter configured to apply a potential, and a control unit configured to determine the initial fill velocity. In particular, a potential was applied to the electrodes of the immunosensor 110, a level of hematocrit was determined, and then the potential was reversed. The concentration of the analyte was subsequently determined in view of the determined level of hematocrit. The level of hematocrit was determined in view of a calculated initial fill velocity.

A plurality of samples were provided for analysis to test the performance of the systems, devices, and methods disclosed herein. The samples were blood samples that contained C-reactive proteins, and thus the concentration of the analyte being determined was the concentration of C-reactive proteins. The samples contained four different levels of hematocrit, which were known so comparisons of the test results could be compared to the actual results to determine the accuracy of the systems, devices, and methods. The four levels of hematocrit were approximately 33%, approximately 41.5%, approximately 47.5%, and approximately 55%. Testing four levels of hematocrit allowed the accuracy of the disclosed systems, devices, and methods to be confirmed over a broad spectrum of concentration levels.

In this first example, an immunosensor was preheated to approximately 37° C. before a sample was introduced. The meter associated with the immunosensor was configured to perform the preheating, although other alternatives could have been used. Samples were then introduced into the immunosensor. While the introduction of samples into the immunosensor could have been accomplished in a variety of manners, in the example each sample was admitted individually by way of capillary action into the fill chamber.

Figure 6:
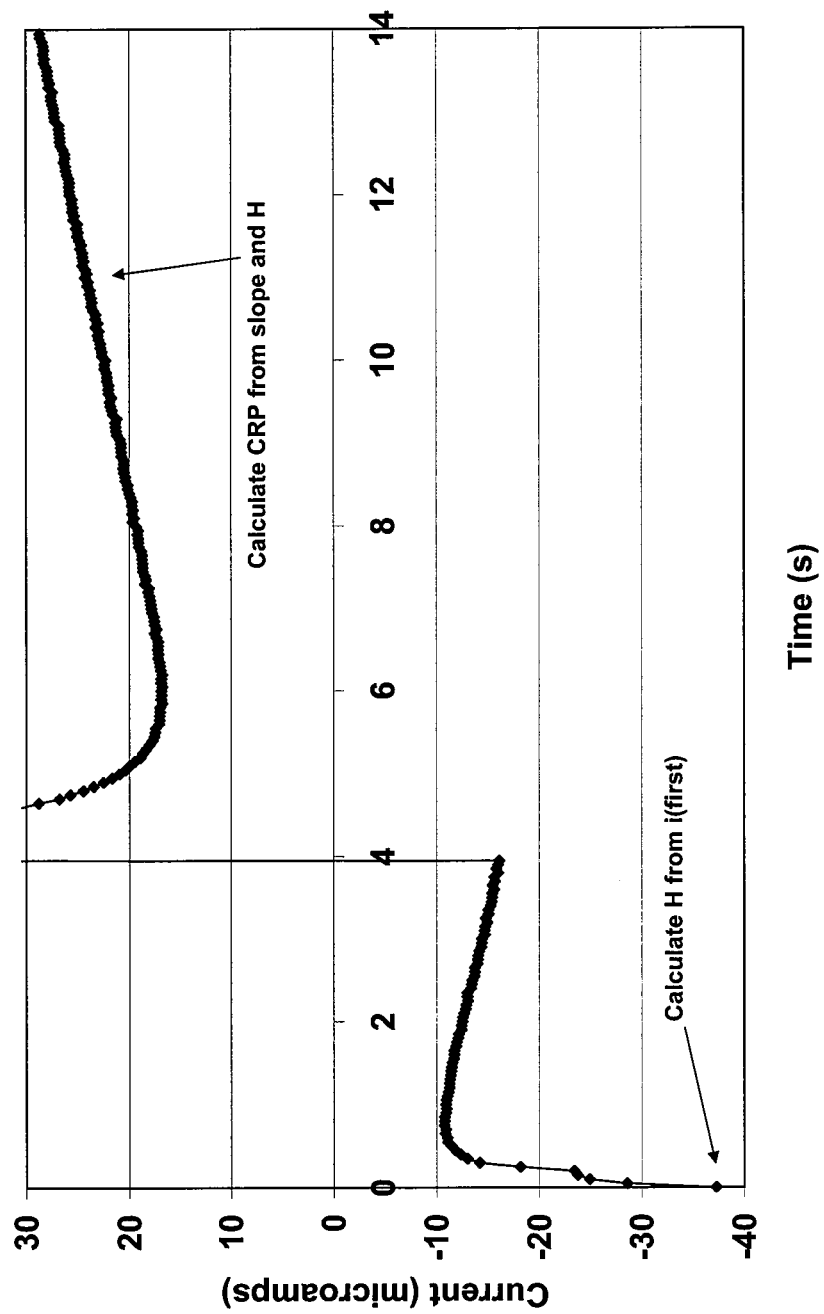
FIG. 6 illustrates a plot of a current versus time transient performed using the device of FIG. 2 in conjunction with one exemplary example for testing a variety of blood samples provided herein.

After approximately two minutes had elapsed, the vent of the immunosensor was accessed by piercing the first sealing component. A piercing instrument of the meter was used to perform the piercing action, which in turn allowed the blood to flow from the reaction chamber of the immunosensor into the detection chamber of the immunosensor. As soon as the blood started to enter the detection chamber, a potential of about 300 mV was applied to the electrodes by way of the meter for approximately four seconds. Alternatively, the potential could have been applied prior to or while the blood was arriving in the detection chamber. Subsequently, the potential was interrupted and reversed for approximately 10 seconds. A plot of the current versus time transient resulting from this example is illustrated in FIG. 6. The initial current for each sample, which in the present example was measured about every 10 milliseconds and then averaged over about the first 50 milliseconds, is related to the hematocrit level of the particular sample. A level of hematocrit is determined from the initial current during the first application of electric potential, while a level of C-reactive protein is calculated following the reversed potential, based on the slope of the current versus time plot and the determined level of hematocrit.

As discussed above, in some embodiments it may be desirable to only measure a level of hematocrit. Thus, the first calculation based on the initial current may be the only step that is needed to make that calculation. While in the present example this determination is made as a result of a four second potential application, the actual determination of the hematocrit level can be determined as quickly as the initial current can be calculated. Thus, by way of non-limiting example, if the initial current is calculated based on an average over about the first 50 milliseconds, the level of hematocrit can be determined following about the first 50 milliseconds. Thus, measurements of a hematocrit level of a blood sample can be performed in less than one second.

Figure 7:
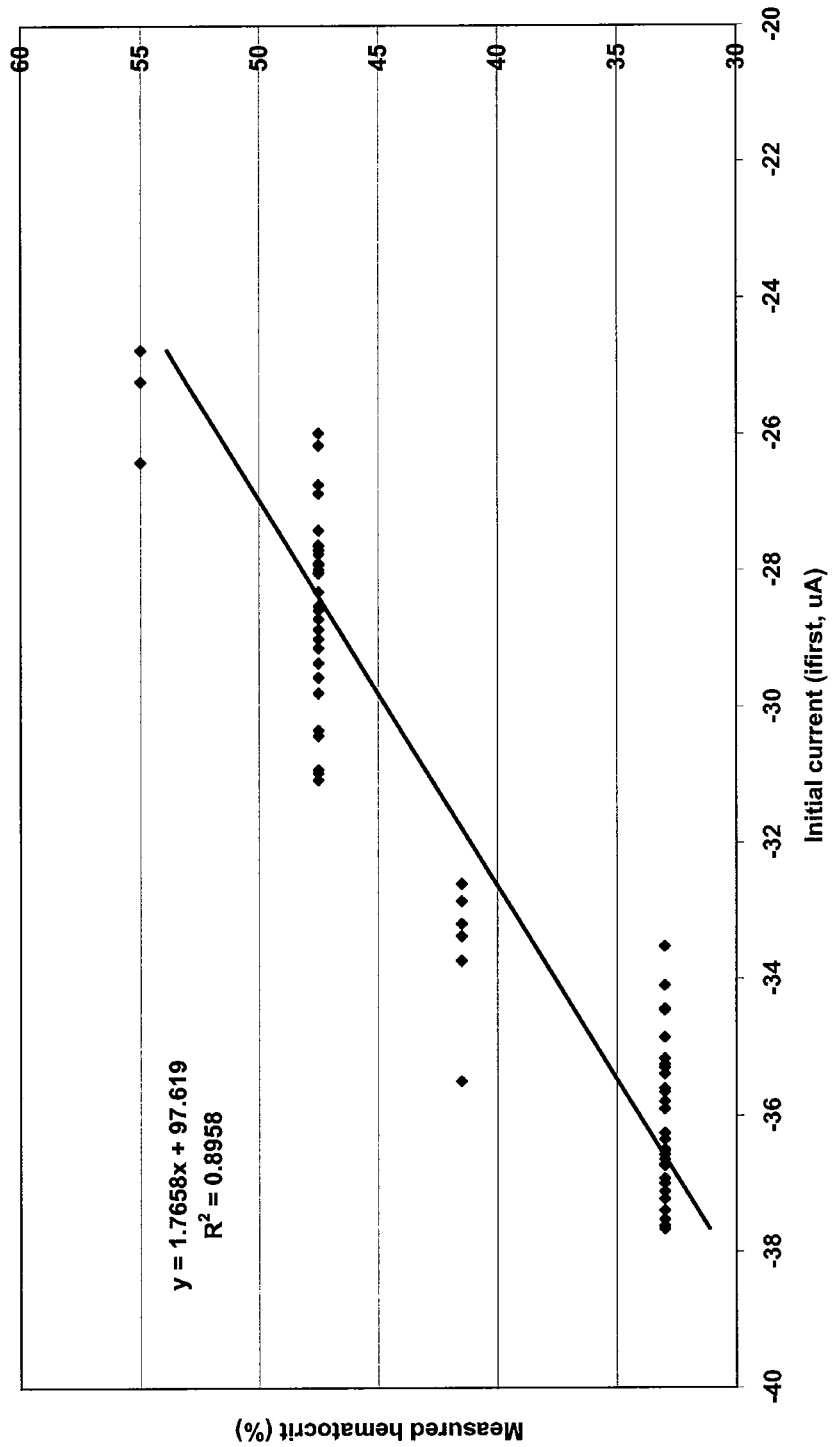
FIG. 7 illustrates a plot of a hematocrit concentration level for each blood sample used in association with the example associated with FIG. 6 versus a current.
Figure 8:
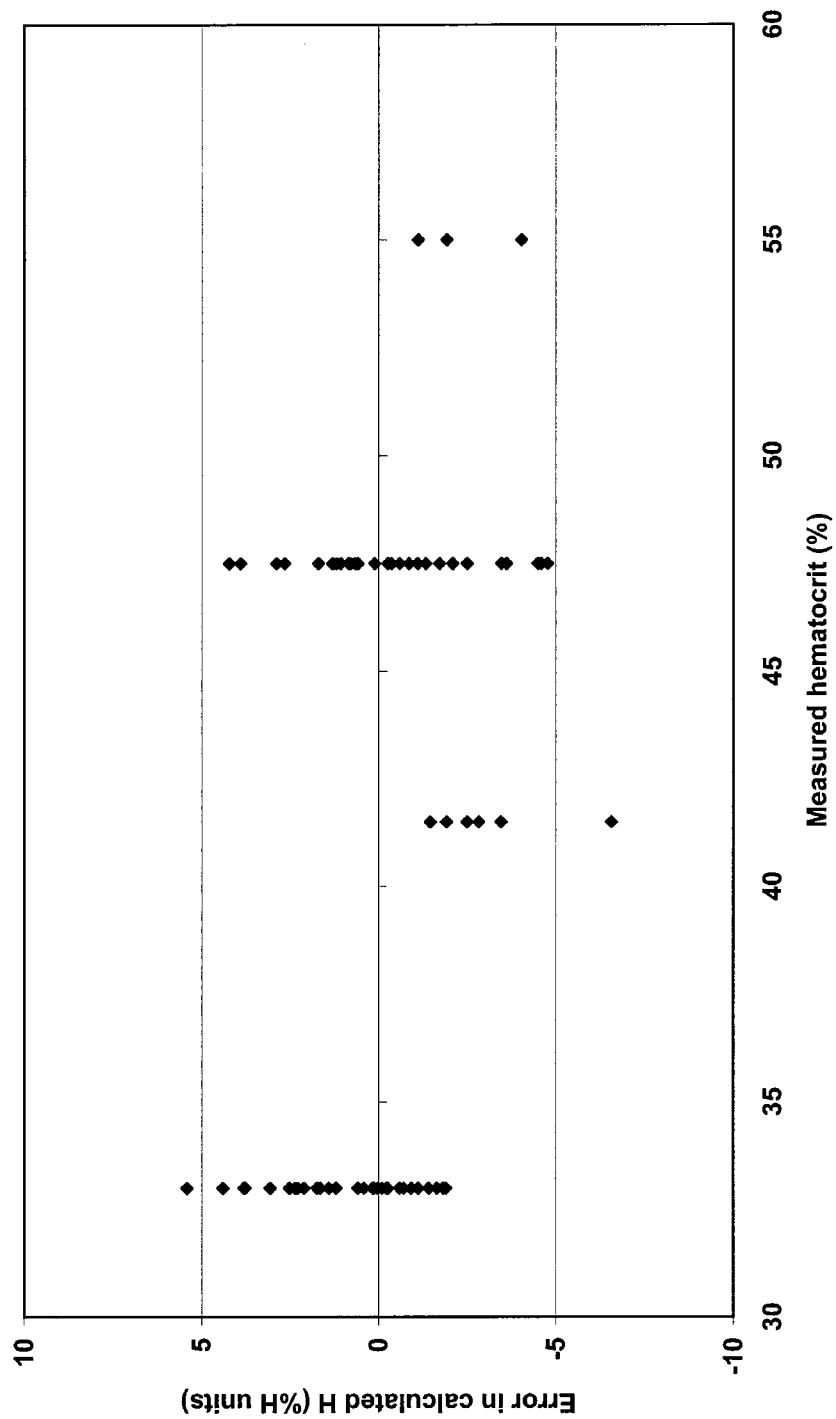
FIG. 8 illustrates a plot of a percent error of the determined hematocrit concentration levels for each blood sample associated with FIG. 6 versus the determined hematocrit concentration levels of each blood sample associated with FIG. 6.

The level of hematocrit for each sample that was determined is illustrated by FIG. 7. FIG. 7 illustrates a plot of the concentration level of the hematocrit for each sample versus the determined initial current. The plot clearly shows that samples containing four different levels of hematocrit were tested, which correlates with the known concentration levels. Further, as illustrated, higher levels of hematocrit generally led to lower absolute values of the measured initial currents. For example, samples having a concentration of hematocrit that was approximately 33% had initial current absolute values that were approximately in the range of about 38 microamperes to about 33 microamperes, while samples having a concentration of hematocrit that was approximately 47.5% had initial current absolute values that were approximately in the range of about 31 microamperes to about 26 microamperes. A best fit line of all of the results was determined, which is also illustrated in FIG. 7. The equation that correlates with the best fit line is:

$$H = 97.6 - 1.7658 |i_t| \quad \text{(Eq. 1)}$$

where H is the level of hematocrit and $|i_t|$ is the initial current. The error between the equation that illustrates the results of the hematocrit level versus initial current and the actual results is illustrated in FIG. 8. More particularly, FIG. 8 plots the percent error that existed in each test sample versus the actual measured hematocrit level. Every actual result but two was within about ±5% of the calculated range, with a substantial amount in the range of about ±2.5%.

Figure 9:
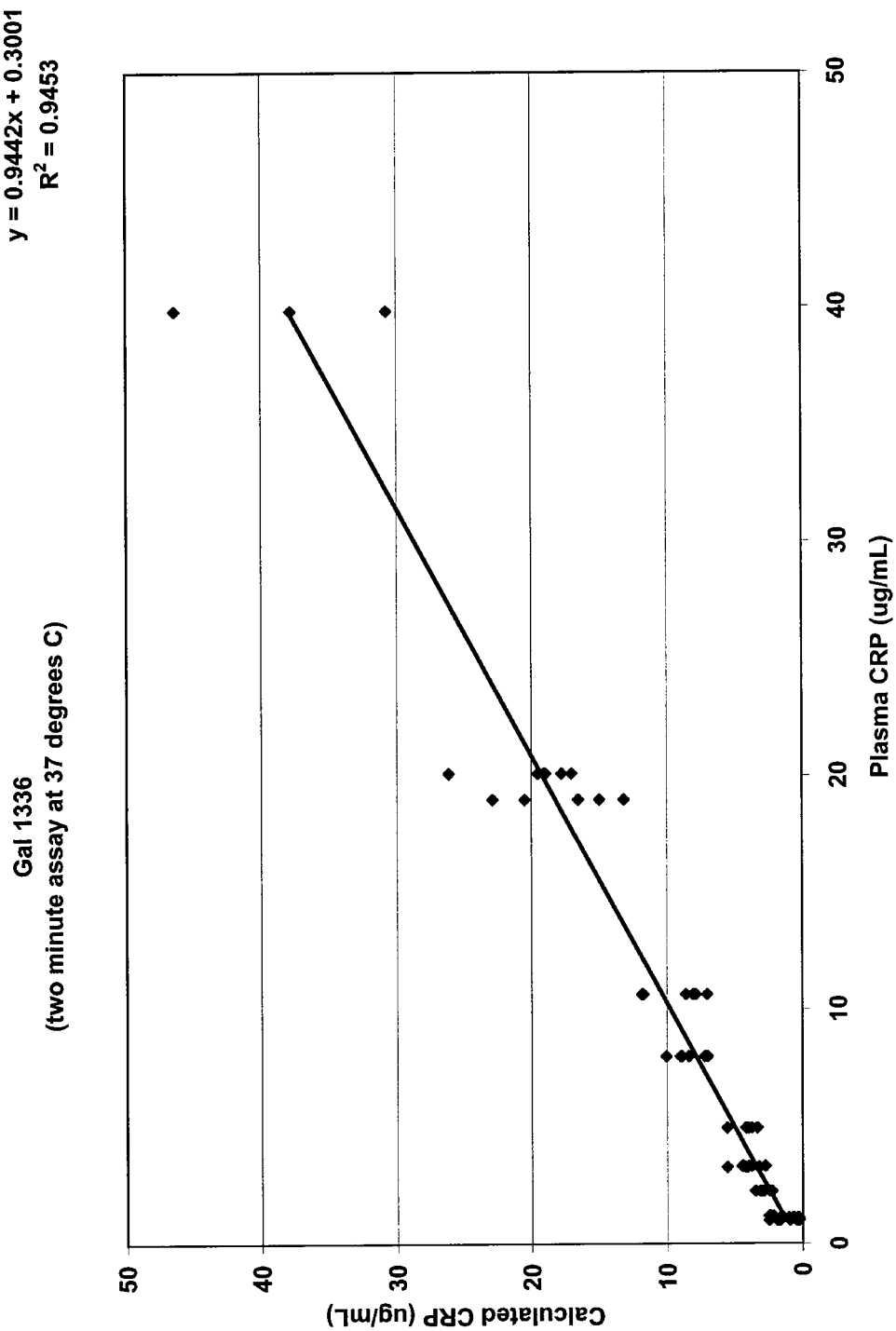
FIG. 9 illustrates a plot of a calculated C-reactive protein level of each blood sample associated with FIG. 6 versus a reference value of plasma C-reactive protein as determined by a conventional enzyme immunoassay.

Once the hematocrit level was determined, that result, along with the slope of the current versus time transient of FIG. 6 approximately between about 9 seconds and about 14 seconds, was used to calculate the value of C-reactive protein in the sample. The level of C-reactive protein was determined by the equation:

$$C_O = -3.5 + 0.866 \exp(y) \quad \text{(Eq. 2)}$$

where $C_O$ is the concentration of C-reactive protein and y is based on the aforementioned slope and the level of hematocrit. More particularly, y removed the effect of hematocrit on the slope and was calculated by the following equation:

$$y = \frac{m}{(1 - 0.01H)^{0.83}} \quad \text{(Eq. 3)}$$

where m is the slope of the current versus time transient approximately between about 9 seconds and about 14 seconds and H is the determined hematocrit level. FIG. 9 illustrates a plot of the calculated C-reactive protein level of each of the samples versus the reference value of plasma C-reactive protein as determined by a conventional enzyme immunoassay. The best fit line in FIG. 9 illustrates an accurate correlation between the determined level of C-reactive protein and the equivalent reference value.

EXAMPLE 2

The use of an electrochemical system to measure an initial fill velocity based on measuring current flow was further demonstrated by another example. The sample analyzing device that was used in this example was also the immunosensor 110 of FIG. 2, a meter configured to apply a potential, and a control unit configured to determine the initial fill velocity. In particular, a potential was applied to the electrodes of the immunosensor 110, a level of hematocrit was determined, and then the potential was reversed. The concentration of the analyte was subsequently calculated in view of the determined level of hematocrit. Similar to the previous example, a number of samples having varying hematocrit levels were used with the system in order to demonstrate the capabilities of the system. The known levels of hematocrit concentration were approximately 33.5%, approximately 41%, approximately 47.5%, and approximately 56.5%.

A sample was introduced into an unheated immunosensor by way of capillary action. The sample entered the fill chamber and moved to the reaction chamber, where it remained for approximately five minutes. The vent of the immunosensor was subsequently opened by piercing the first sealing component, thereby allowing the blood of the sample disposed in the immunosensor to flow from the reaction chamber of the immunosensor into the detection chamber of the immunosensor. Allowing the sample to wait longer before piercing at least one of the sealing components provided adequate time for the antigen and the antibody-enzyme conjugate of the immunosensor to diffuse and react, particularly in view of the unheated reaction chamber. Preheating the immunosensor can speed this time up, as demonstrated by Example 1 above. In the present example, however, no heating component was included, which provided the benefits of eliminating complications and costs associated with incorporating a heating element with the system. In such instances where a temperature of a chamber is not known or constant, however, the calculations performed to determine levels of hematocrit and/or levels of C-reactive protein should account for the effect of different ambient temperatures in order to provide more accurate results. Such accounting was provided for in this second example. In one embodiment, the temperature of the sample can be inferred.

Similar to the earlier example, as the blood started to enter the detection chamber, a potential of approximately 300 mV was applied to the electrodes by way of the meter for approximately 4 seconds. Subsequently, the potential was interrupted and reversed for approximately 10 seconds. A plot of the resulting current versus time transient was created in a manner similar to the plot illustrated in FIG. 6. From the resulting plot, a level of hematocrit was determined from the initial current during the first application of electric potential. Subsequently, a level of C-reactive protein was calculated following the reversed potential. The calculated level of C-reactive protein was based on the slope of the current versus time plot and the determined level of hematocrit. Accounting for the temperature in this example provided further accuracy, as shown below.

Figure 10:
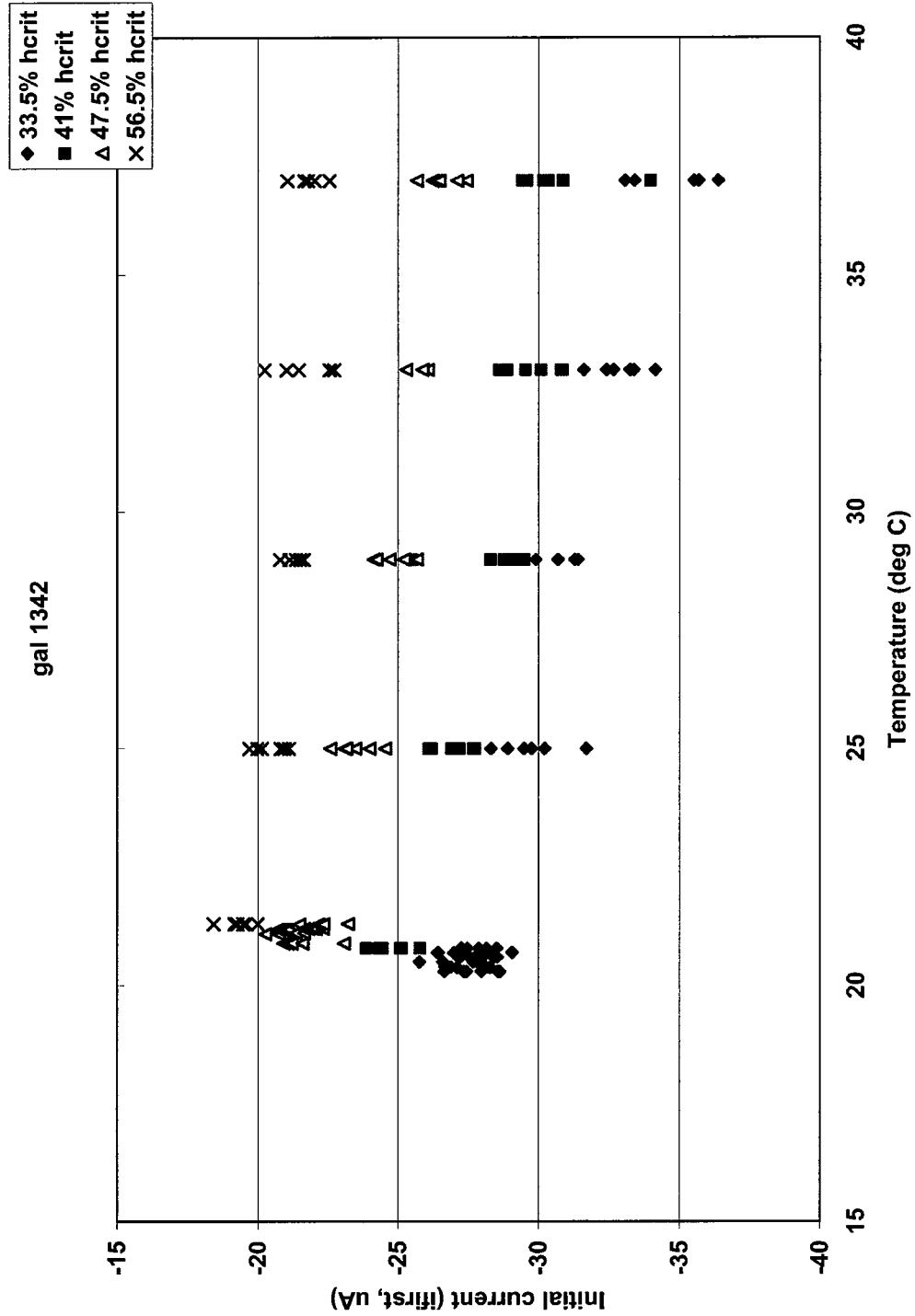
FIG. 10 illustrates a plot of a current versus a temperature of a detection chamber of the immunosensor in which the blood samples are disposed performed using the immunosensor of FIG. 2 in conjunction with another exemplary example for testing a variety of blood samples provided herein.
Figure 11:
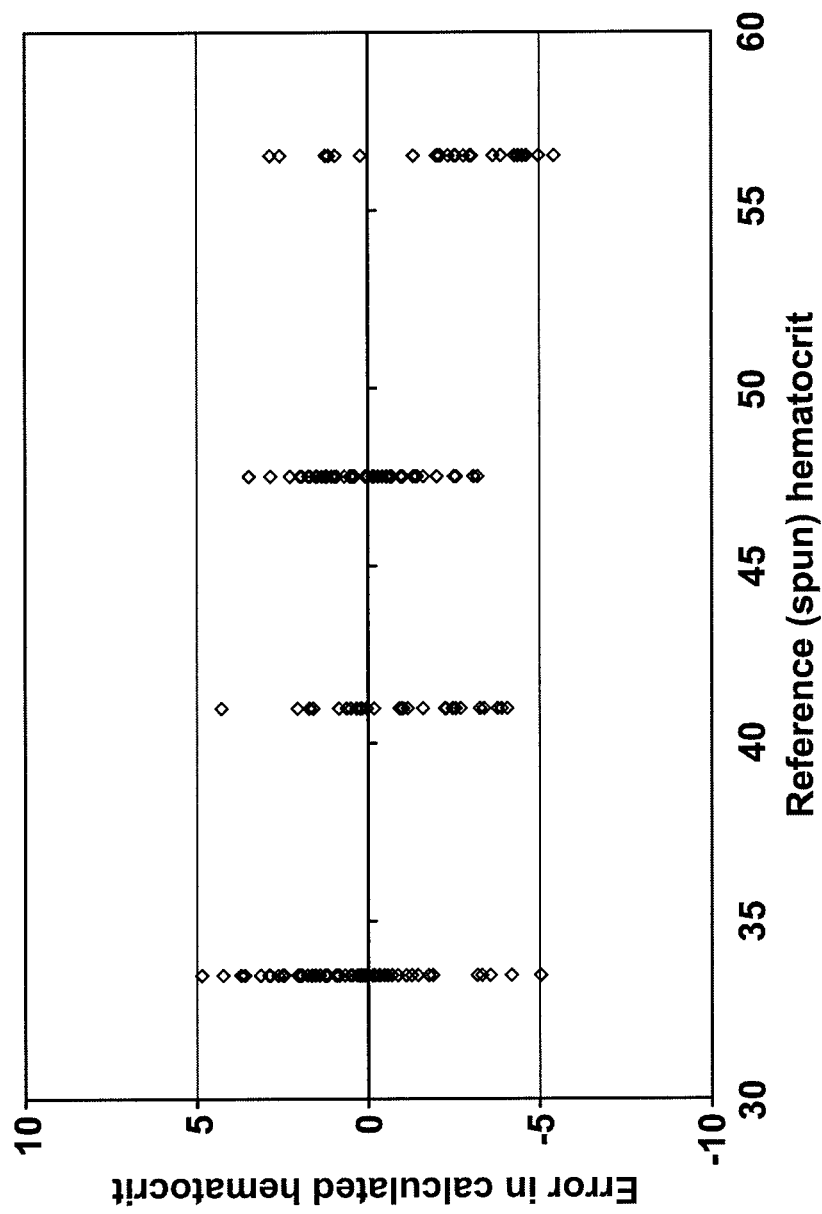
FIG. 11 illustrates a plot of a percent error of the determined hematocrit concentration levels for each blood sample associated with FIG. 10 versus the determined hematocrit concentration levels of each blood sample associated with FIG. 10.

The initial current that was determined for each sample is illustrated by FIG. 10. FIG. 10 illustrates a plot of the determined initial current versus the temperature of the detection chamber of the immunosensor in which the sample was disposed. The initial currents for the four types of samples (i.e., the four different levels of hematocrit) were measured over a range of approximately 20° C. to approximately 37° C. Generally, higher levels of hematocrit led to lower absolute values of the initial current. As temperatures in the chamber increased, the absolute values of the initial current also generally increased. As shown, the initial current varied linearly with temperature when the hematocrit was fixed. In view of the temperature of the chamber and the initial current, the level of hematocrit was determined by the following equation:

$$H = 77.1 - 2.1|i_i| + 0.75T \quad \text{(Eq. 4)}$$

where H is the level of hematocrit, $|i_i|$ is initial current, and T is the temperature of the detection chamber. Similar to the earlier example, the errors in the estimated levels of hematocrit were approximately within ±5%, as shown in FIG. 11. FIG. 11 plots the percent error that existed in each test sample versus a reference hematocrit level of that sample. Also similar to the earlier example, in some embodiments only a hematocrit value determination is made, thereby allowing for quick assessments of various medical conditions that can be evaluated based on hematocrit value determinations.

Once the hematocrit level was determined, that result, along with the slope of the current versus time transient approximately from about 9 seconds to about 14 seconds and the temperature of the detection chamber, were used to calculate the value of C-reactive protein in the sample. The level of C-reactive protein was determined by the equation:

$$C_O = -5.7 + 1.78 \exp(y') \quad \text{(Eq. 5)}$$

where $C_O$ is the concentration of C-reactive protein and y' is based on the temperature of the detection chamber and a variable y, which in turn is based on the aforementioned slope and the level of hematocrit. More particularly, y' removed the effect of temperature on slope and was calculated by the following equation:

$$y' = \frac{y}{1 + 0.068(T - 25)} \quad \text{(Eq. 6)}$$

where T is the temperature of the detection chamber of the immunosensor and y is a term that removes the effect of hematocrit on the slope. The equation for y' assumes that the slope changes by a certain percentage, typically approximately in the range of about four to about seven percent, for approximately every one degree ° C. change in temperature. Further, the term T −25 corrects all values of y' to a standard temperature of 25° C. If a different temperature should be corrected for, this term can be adjusted accordingly. In fact, one skilled in the art will recognize many ways to manipulate this equation, and the other equations disclosed throughout this disclosure, for other samples, temperatures, etc.

The variable y was calculated by the following equation:

$$y = \frac{m}{(1 - 0.01H)^{1.55}} \quad \text{(Eq. 7)}$$

where m is the slope of the current versus time transient approximately between about 9 seconds and about 14 seconds and H is the determined hematocrit level. The term (1-0.01 H) represents a fraction of the volume that is plasma that is then raised to an arbitrary power. The power can be obtained as a calibration coefficient.

Figure 12:
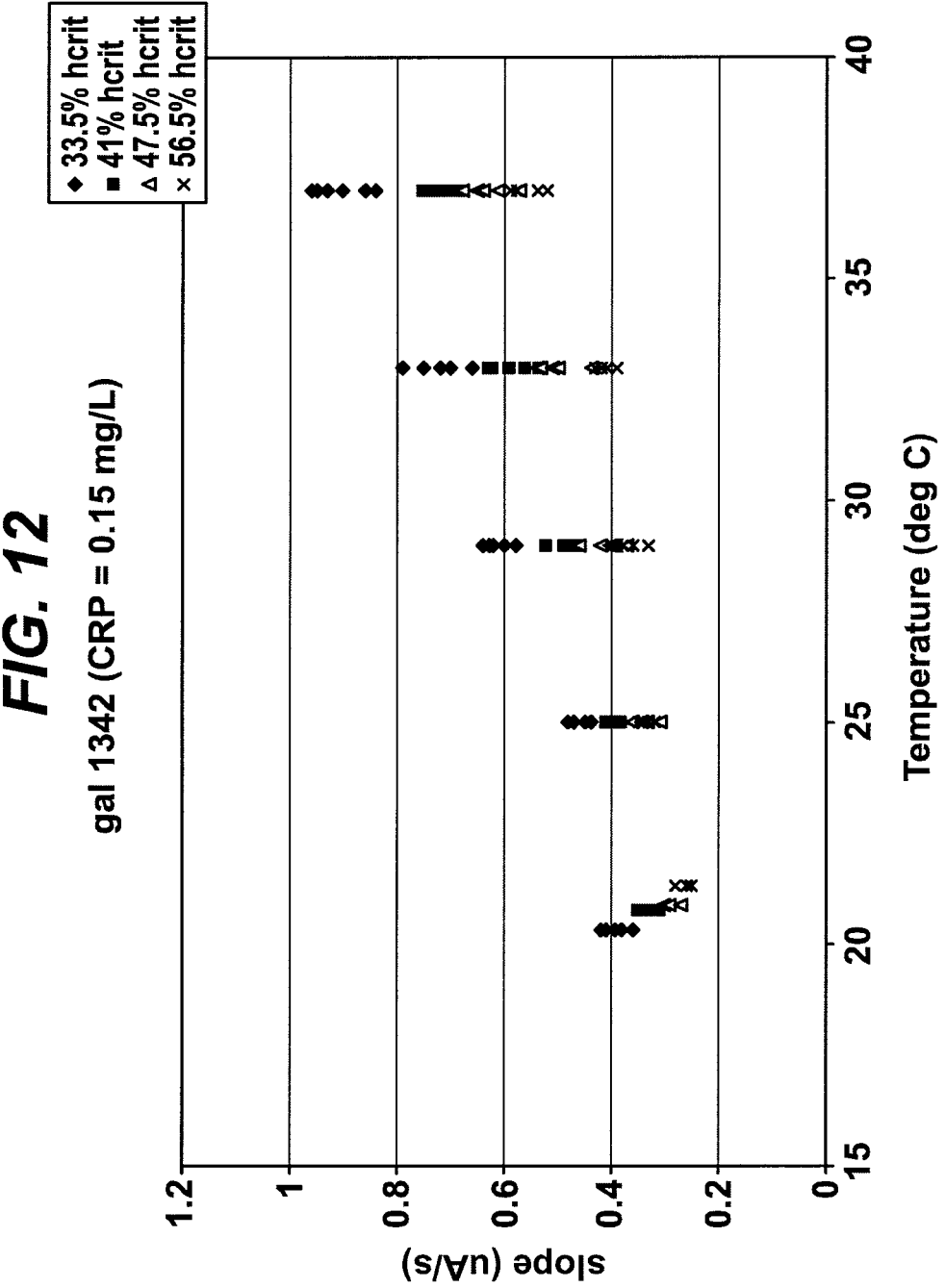
FIG. 12 illustrates a plot of a determined slope based on a change in current over time for each blood sample associated with FIG. 10 versus a temperature of a detection chamber of the immunosensor in which the blood samples are disposed.

The slope of the transient approximately between about 9 seconds and about 14 seconds was a function of C-reactive protein, a hematocrit level, and the temperature. When the concentration of C-reactive protein was fixed at approximately 0.15 mg/L, there was still a considerable variation of the slope with respect to hematocrit and temperature, as shown in FIG. 12. FIG. 12 illustrates a plot of the determined slope versus the temperature of the detection chamber of the immunosensor in which the sample was disposed. Initial currents for each of the four hematocrit level samples were measured over a range of approximately 20° C. to approximately 37° C. Generally, the greater the level of hematocrit in a sample, the lower the value of the slope. As temperatures in the chamber increased, the values of the slope generally increased.

Figure 13:
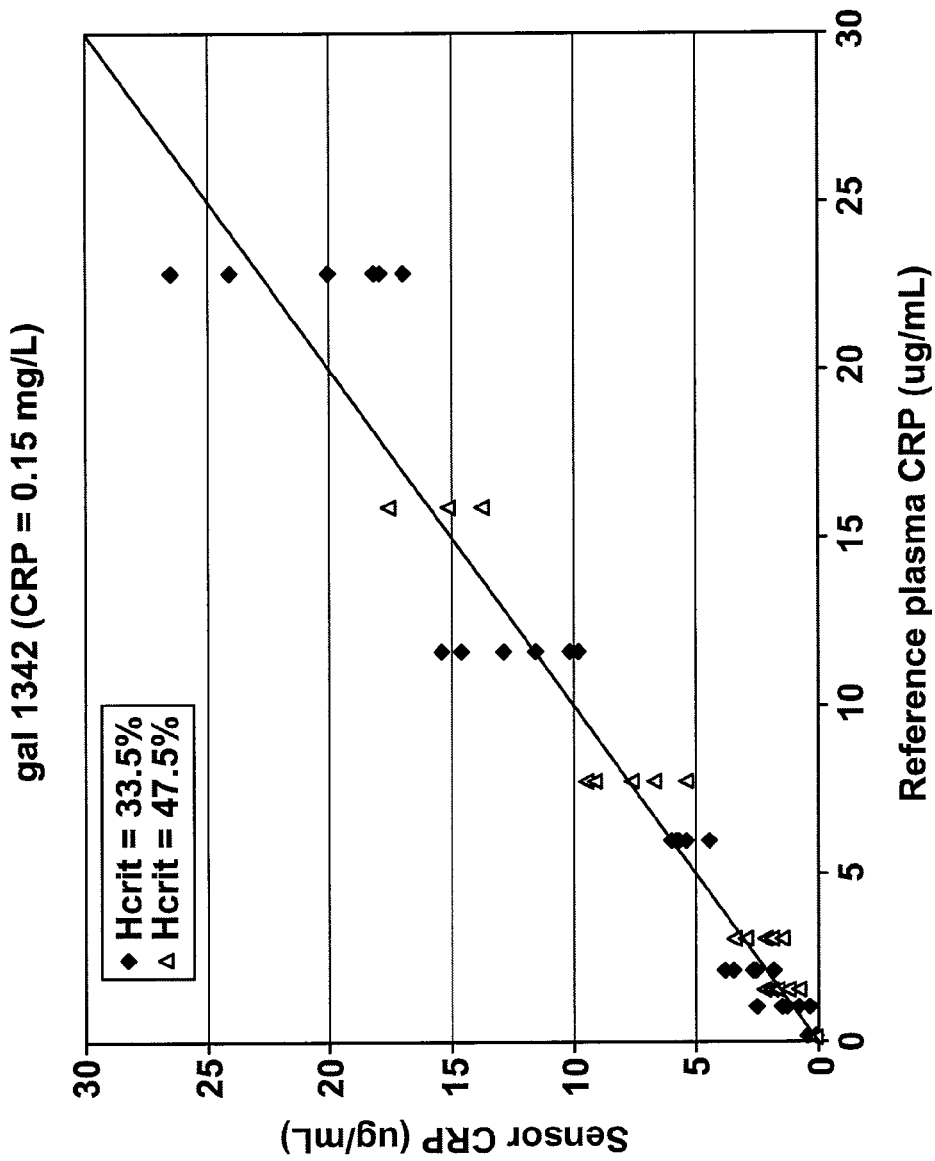
FIG. 13 illustrates a plot of a calculated C-reactive protein level of blood samples associated with FIG. 10 having approximately a 33.5% hematocrit level and approximately a 47.5% hematocrit level versus a reference value of plasma C-reactive protein as determined by a conventional enzyme immunoassay.

FIG. 13 illustrates a plot of the calculated C-reactive protein level of each of the samples having a hematocrit level of approximately either about 33.5% or about 47.5%, versus the reference value of plasma C-reactive protein as determined by a conventional enzyme immunoassay. The best fit line in FIG. 13 illustrates an accurate correlation between the determined level of C-reactive protein and the equivalent reference value.

One skilled in the art will appreciate that these two examples are merely two of many examples of how the teachings contained herein can be performed and used. Further, although the methods, systems, and devices disclosed herein are primarily used in conjunction with determining a concentration of an analyte of a blood sample, and are primarily focused on accounting for errors that can result from varying levels of hematocrit in blood samples, one skilled in the art will recognize that the disclosures contained herein can also be used for a variety of other samples containing analytes and can test for a variety of antigens and/or antibodies contained within a sample.

One skilled in the art will also recognize that to the extent various methods, systems, and devices rely on a particular equation, the equations provided are generally based on the examples to which the equations were applied. One skilled in the art, in view of the present disclosure, will be able to make adjustments to the disclosed equations for other situations without departing from the scope of the invention.

Still further, the methods discussed herein, such as those related to determining a concentration and using the systems and devices, are also not limited by the particular steps or order of the steps, except where indicated. One skilled in the art will recognize various orders in which the methods can be performed, and further, will recognize that steps can be modified or added without departing from the scope of the invention.

Non-limiting examples of some of the other types of devices with which the methods disclosed herein can be used are discussed in greater detail in U.S. Pat. No. 5,942,102 of Hodges et al., entitled "Electrochemical Method" and filed on May 7, 1997, U.S. Pat. No. 6,174,420 of Hodges et al., entitled "Electrochemical Cell" and filed on May 18, 1999, U.S. Pat. No. 6,379,513 of Chambers et al., entitled "Sensor Connection Means" and filed on Sep. 20, 1999, U.S. Pat. No. 6,475,360 of Hodges et al., entitled "Heated Electrochemical Cell" and filed on Sep. 11, 2000, U.S. Pat. No. 6,632,349 of Hodges et al, entitled "Hemoglobin Sensor" and filed on Jul. 14, 2000, U.S. Pat. No. 6,638,415 of Hodges et al., entitled "Antioxidant Sensor" and filed on Jul. 14, 2000, U.S. Pat. No. 6,946,067 of Hodges et al., entitled "Method of Forming an Electrical Connection Between an Electrochemical Cell and a Meter" and filed on Dec. 9, 2002, U.S. Pat. No. 7,043,821 of Hodges, entitled "Method of Preventing Short Sampling of a Capillary or Wicking Fill Device" and filed on Apr. 3, 2003, and U.S. Pat. No. 7,431,820 of Hodges et al., entitled "Electrochemical Cell" and filed on Oct. 1, 2002, each of which is hereby incorporated by reference in its entirety.

Further, to the extent the disclosures herein are discussed for use with a device having a particular configuration, any number of configurations can be used. For example, some configurations that can be used with the present disclosures include sensors having two electrodes facing each other, sensors having two electrodes on the same plane, and sensors having three electrodes, two of which are opposed and two of which are on the same plane. These different configurations can occur in any number of devices, including immunosensors and the other aforementioned devices.

Various aspects of the devices, systems, and methods can be adapted and changed as desired for various determinations without departing from the scope of the present invention. Further, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for determining an analyte of a whole blood sample, the method comprising the steps of:
 providing a sample of whole blood to a sample analyzing device having a capillary space;
 measuring an initial fill velocity of the sample in at least a portion of the capillary space in which the initial velocity is measured by:
  applying an electrical potential;
  measuring an electrical current; and
  determining an initial current flow;
 determining a hematocrit value of the blood sample solely from the measured initial fill velocity using an equation that requires the determined initial current flow and wherein the sample includes an analyte, and
 calculating a concentration of the analyte by:
  applying an electric potential;
  measuring an initial current after applying the electric potential;
  reversing the electric potential;
  measuring a change in current over time following the reversal of the electric potential as a slope (m) of a current versus time graph; and
  using an equation that requires the determined hematocrit value and the measured change in current over time.

2. The method of claim 1, wherein the step of measuring an initial fill velocity further comprises the additional steps of:
 performing current measurements approximately every 10 milliseconds for at least approximately 50 milliseconds; and
 calculating an average current based on the current measurements.

3. The method of claim 1, wherein the step of measuring an initial fill velocity of the sample occurs after the sample enters the capillary space.

4. The method of claim 1, wherein the step of measuring an initial fill velocity of the sample occurs after the sample crosses into a region of the capillary space of the sample analyzing device where a detection signal is generated.

5. The method of claim 1, further comprising the step of at least one of measuring a temperature of the sample and inferring a temperature of the sample.

6. The method of claim 1, wherein the sample analyzing device is an immunosensor.

7. The method of claim 1, further comprising the step of at least one of measuring a temperature of the sample and inferring the temperature of the sample.

8. The method of claim 7, further comprising the step of measuring a change in current over a period of time after the step of reversing the electric potential, wherein the step of calculating a concentration of the analyte comprises the additional step of calculating the concentration of the analyte in view of the change in current over the period of time and temperature of the sample.

9. The method of claim 1, wherein the equation for determining the hematocrit value is $$H = 97.6 - 1.7658 |i_i|$$

in which $|i_i|$ is the absolute value of the initial current.

10. The method of claim 5, including the equation for determining the hematocrit value is $$H = 77.1 - 2.1 |i_i| + 0.75 T$$

in which $|i_i|$ is the absolute value of the initial current and T is the temperature of the sample.

11. The method of claim 1, in which the equation for determining analyte concentration is $C_O = -3.5 + 0.866 \exp(y)$ in which $C_O$ is the concentration of analyte and $$y = \frac{m}{(1 - 0.01H)^{0.83}}$$

in which m is the slope of the current versus time curve, and H is the determined hematocrit value.

12. The method of claim 8, in which the equation for determining analyte concentration is $C_O = -5.7 + 1.78 \exp(y')$ in which $C_O$ is the concentration of the analyte and $$y' = \frac{y}{1 + 0.068(T - 25)},$$

in which T is the temperature of the sample and $$y = \frac{m}{(1 - 0.01H)^{1.55}}$$

and
 m is the slope of a current versus time curve and H is the determined hematocrit value.

* * * * *